United States Patent [19]

Chang et al.

[11] Patent Number: 5,643,743

[45] Date of Patent: *Jul. 1, 1997

[54] **METHOD FOR DETECTING COLIFORM AND *E. COLI* BACTERIA**

[75] Inventors: George W. Chang, Berkeley; Rosalind A. Lum, Saratoga, both of Calif.

[73] Assignee: The Regents of the University of California, Oakland, Calif.

[*] Notice: The term of this patent shall not extend beyond the expiration date of Pat. No. 5,411,867.

[21] Appl. No.: 365,884

[22] Filed: Dec. 29, 1994

Related U.S. Application Data

[63] Continuation of Ser. No. 91,528, Aug. 12, 1993, Pat. No. 5,411,867, which is a continuation-in-part of Ser. No. 523,320, May 14, 1990, abandoned.

[51] Int. Cl.⁶ .................. C12Q 1/04; C12Q 1/10; C12N 1/20
[52] U.S. Cl. .................. 435/34; 435/38; 435/252.8; 435/253.6
[58] Field of Search .................. 435/18, 29, 34, 435/38, 252.8, 253.6, 968

[56] References Cited

U.S. PATENT DOCUMENTS

| | | | |
|---|---|---|---|
| 3,870,601 | 3/1975 | Warren | 195/103 JR |
| 4,245,043 | 1/1981 | Lund | 435/33 |
| 4,591,554 | 5/1986 | Koumura | 435/18 |
| 4,925,789 | 5/1990 | Edberg | 435/38 |
| 5,411,867 | 5/1995 | Chang | 435/18 |

OTHER PUBLICATIONS

Difco Manual, Difco Labs Detroit MI 10th Ed 1984 pp. 321–322.

Edberg S, Comparison of β–Glucuron, Dase–Based . . . J. of Clin Micro vol. 24 No. 3 1986 pp. 368–371.

Edberg S, National Field Evaluation of a Defined . . . App & Environ Micro vol. 54 No. 6 1988 pp. 1595–1601.

*Primary Examiner*—Ralph Gitomer
*Attorney, Agent, or Firm*—Richard Aron Osman

[57] ABSTRACT

A novel highly sensitive method for detection of the presence of total coliform and *E. coli* in water samples, food products, and seafood employs a new type of media having composition which allows an unequivocal detection of very small number of *E. coli*. The new low pH media which contain trimethylamine-N-oxide promote the growth of chlorine or food processing injured *E. coli* for their easier detection.

19 Claims, 2 Drawing Sheets

METHOD FOR DETECTING COLIFORM AND *E. COLI* BACTERIA

BACKGROUND OF INVENTION

This is a continuation, of application Ser. No. 08/091,528, filed Aug. 12, 1993, now U.S. Pat. No. 5,411,867 which is a continuation-in-part of the pending patent application entitled "Novel and Improved Method for Determination of *E. coli* in Water", Ser. No. 07/523,320, filed on May 14, 1990 now abandoned.

FIELD OF THE INVENTION

This invention concerns a novel highly sensitive method for detection of the presence of total coliform and *E. coli* in water samples, food products, and seafood. Particularly, this invention concerns the method which employs new type of media having composition which allows an unequivocal detection of very small number of *E. coli*. The new media promote the growth of chlorine or food processing injured *E. coli* for their easier detection. This invention also concerns the low pH, trimethylamine-N-oxide containing media and the method for sole detection of *E. coli* in water, in food products and in seafood.

BACKGROUND AND RELATED DISCLOSURES

*Escherichia coli* (*E. coli*) is a type species of *Escherichia* genus of *Enterobacteriaceae* family. *E. coli* is a gram-negative facultatively anaerobic bacteria normally inhabiting a gastrointestinal tract which bacteria is found in human and animal feces. *E. coli* is a frequent cause of infections of the urogenital tract and diarrhea.

Since *E. coli* is normally found in feces, its presence in the water or food stuff has been long recognized and used as an indicator of possible fecal contamination of water and food. Therefore, much effort has been expended in devising and improving methods for detection, identification and quantitation of these bacteria.

The use of *E. coli* as a water contamination indicator is disadvantaged, as there is no simple and specific way for their detection. Instead, coliform bacteria, a broader subset of species *Enterobacteriaceae*, which includes certain environmental organisms as well as fecal *E. coli*, but excludes *Salmonella*, *Shigella* and *Proteus* are usually detected. Consequently, coliform bacteria became a measure of a drinking water contamination by fecal matter.

Thus, it would be advantageous to have available an accurate test for determination of the presence of *E. coli*. While there are available tests for determination of *E. coli*, such tests are not very accurate and may have a false positive or negative false error up 30–40%.

Currently available tests for determination of presence of coliforms and in particular *E. coli* are based on characterization tests which place the unknown organism in a defined group. Most commonly used tests are enzymatic tests where the presence of an enzyme known to be involved in the bacteria metabolism is detected subjectively by observation of a change in the appearance, a change in the color, a change in the fluorescence or some other chemical indication. *Methods in Microbiology*, 19: 105 (1987).

Most of the existing tests for coliform and for *E. coli* are based on the last century findings described in *Forsch. Med*, 3: 515 (1885), that Escherichia ferments glucose and lactose and produces gas or acid as a result of such fermentation. Most of the currently used methods utilize enzymes involved in the metabolism of lactose, such as, for example, the coliform bacterial enzyme β-D-galactosidase which catalyzes the first step in the conversion of lactose to acid and gas.

Attempts to detect the presence of *E. coli* and differentiate it from other coliform early in the 20th century led to a classical fecal coliform (thermotolerant coliform) test involving incubation of bacterial cultures at 44.5° C. At this temperature, most environmental coliforms will not grow but *E. coli* will grow and produce gas or acid from lactose.

Two primary disadvantages are associated with the fecal coliform technique. First, the procedure is lengthy. Second, due to rather high temperatures of above 44° C. which must be used for bacterial incubation, the procedure is often lethal for stressed or injured bacteria. Since most of the drinking water is treated with chlorine which inevitably stresses and injures the *E. coli* cell membrane, under the normal circumstances the use of temperature over 44° C. is not feasible.

To avoid this problem, it is customary to inoculate fecal coliform tubes with fully grown cultures from a presumptive coliform test. Such procedure takes two days. Alternatively, fecal coliform tubes may be incubated for a short while at 35° C. followed by 44.5° C. incubation. However, the gain in the shortening the test time is outweighed by additional manipulation involving timing of two incubations and additional handling. Second, as described in *Appl. Environ. Microb.*, 55: 335 (1989), the fecal coliform procedure has a limited specificity because it recognizes certain percentage of coliforms which are not *E. coli* as undesirable and harmful *E. coli* and thus results in false positive identification of *E. coli* where there is none.

In the clinics, many attempts to develop better tests for screening of fully grown pure colonies of pathogenic members of the family *Enterobacteriaceae* were made. In 1984, *J. Clin. Microbiol.*, 20: 136, described a single tube, multiple test medium for identification of fully grown pure cultures of *Enterobacteriaceae* from enteric and other clinical specimens. The medium used in that test allows detection of motility, β-galactosidase, phenylalanine deaminase activity and hydrogen sulfide and indole production. However, the test can be done only on fully grown pure colonies and is thus not useful for water samples.

Lately, the presence of β-glucuronidase (GUR) became a recognized indicator of the presence of *E. coli*. In 1976, *Acta Pathol. Microbiol. Scand. Sect. B*, 84: 245 (1976) described findings showing that 97% of clinical isolates of *E. coli* produce β-D-glucuronidase (GUR), whereas most other coliform bacteria do not. The success of GUR on clinical samples motivated scientists to apply it for *E. coli* detection in food and water.

One very serious flaw of the β-glucuronidase procedure is that it presumes that all *E. coli* are able to produce β-D-glucuronidase. Based on this presumption, a number of techniques, including the Rapid Identification Method (RIM) and Rapid Detect *E. coli* (RDA) for *E. coli* were developed for fully grown pure cultures of *E. coli*. The RIM technique, referenced below, involves simultaneous measurements of β-glucuronidase and β-galactosidase, followed by separate determination of the presence of indole. However, the technique does not allow the detection of weak or chlorine injured and MUG-negative *E. coli* and thus could result in approximately 30–40% false negative detection error if it were used to identify fecal *E. coli*.

A test for identifying fully grown pure cultures of *E. coli*, described in *J. Clin. Mirobiol.*, 18: 1287 (1983), consists of adding O-nitrophenyl-β-D-galactopyranoside (ONPG) in Sorensen phosphate buffer having pH 7.5, to a fully grown test isolate and incubating the mixture for 1 hour at 35° C. The presence or absence of E. coli is determined by presence or absence of a yellow color which indicates the presence of β-galactosidase. If there is no color change in the original colorless solution, results are read as negative, and the sample is presumed not to contain coliform bacteria such as E. coli.

Two subsequently developed RIM and RDE tests are based on determination of β-glucuronidase. While both these tests are recognized for detection of E. coli, they require fully grown colonies and are quite unsuitable for determination of small numbers of E. coli. Moreover, they are quite unable to detect E. coli which are injured by the chlorination or by the food processing. Both RIM and RDE tests are useful for determination of massive fecal E. coli contamination seen in hospitals but quite unsuitable for detection of small numbers of weak or injured E. coli typically occurring in drinking water treated with chlorine or following the food processing. Moreover, both tests are technically demanding and complicated.

The RIM system consists of reagents-impregnated cotton swabs on wooden sticks with which fully grown bacterial colonies are touched and the swab containing the bacterial inoculum is placed in specific RIM buffer containing ONPG, and incubated at 35° C. The positive ONPG reaction, noted as the development of the yellow color, is followed by the determination of the presence of β-glucuronidase activity by detecting the fluorescence upon irradiation with 366 nm UV light. If the β-glucuronidase test is positive, Kovacs reagent is added for determination of indole presence indicated by red color.

The RDE test is a somewhat improved system for determination of β-glucuronidase which utilizes a paper disk impregnated with substrates. In RDE, fully grown bacterial colonies are inoculated into distilled water to yield a bacterial suspension. Then, a disk containing both β-glucuronidase and ONPG substrates are added to the tube which is incubated at 35° C. Development of yellow color indicates the presence of β-galactosidase, which hydrolyzes the synthetic substrate ONPG. Hydrolysis of ONPG indicates the presence of β-galactosidase and thus the presence of lactose-fermenting organisms like Escherichia A-D group, Citrobacter, Klebsiella, and Enterobacter. When the β-galactoside test is positive, the presence of β-glucuronidase is determined, as in the RIM test, by the examination of the tube with a 366 nm UV light source. If there is a fluorescence, β-glucuronidase is present. If the fluorescence is present, an indole indicator is then added as a third test to the sample to test for indole production. A red color indicates the presence of indole. Only when all three tests, i.e., ONPG, β-glucuronidase and indole are positive, it is concluded that an organism is presumably E. coli. If any of the three tests is negative, the test is interpreted as denoting an organism having a low probability of being E. coli. In such an event, alternative procedures for confirmatory identification of clinical isolates are recommended and performed. J. Clin. Microbiol., 24: 368 (1986).

Both RIM and RDE tests require purified, fully grown colonies and three independent indicators to be positive to determine the presence of E. coli. Consequently, such, determination is still possible only in massively contaminated samples when E. coli is not injured by treatment or processing.

According to some earlier data published in Acta Pathol. Microbiol. Scand. Sect. B, 84: 245 (1976), it was previously believed that β-glucuronidase is present in about 97% of all clinical isolates of E. coli. The observation that about 97% of all clinical E. coli produce β-glucuronidase led to the assumption that 97% of all E. coli from any source produce the enzyme. Recently, however, it has been found that the presumption of 97% glucuronidase-positive E. coli was false. New findings show that only about 66–70% of all E. coli from fecal samples are β-glucuronidase-positive and about 30–34% of E. coli are β-glucuronidase-negative.

These findings have recently been published in Appl. Environ. Microbiol., 55: 335 (1989) showing that first, about 30–34% of all fecal isolates of E. coli are β-D-glucuronidase-negative when measured with lauryl sulfate tryptose broth containing MUG, and second, among those β-glucuronidase-positive E. coli, there is certain number of β-glucuronidase-positive bacteria which are temperature dependent for β-glucuronidase production. In these temperature dependent E. coli, such β-glucuronidase production is rather weak at 37° C. but strongly positive at 44.5° C. Moreover, some fecal samples seem to contain only β-glucuronidase-negative E. coli. Since the samples analyzed in the above study came from the fecal samples of healthy subjects, it is clear that the fecal contamination of water by E. coli may not be detected in around 30–35% of the time when currently available tests described above are used.

The previously accepted 97% glucuronidase-positive E. coli premise led consequently to a development of so called MMO-MUG (Minimal Medium ONPG-methylumbelliferyl-β-D-glucuronidase) test currently approved by EPA as one of the analytical methods to enumerate total coliform.

The MMO-MUG test uses a medium containing a combination of ONPG and a fluorogenic compound MUG as a β-glucuronidase substrate. The test is based on introducing a tested sample into the MMO-MUG medium and on observation of the production of β-galactoside from ONPG, as evidenced by the formation of a yellow color in 24 hours, followed by development of a fluorescence due to metabolism of 4-methylumbelliferyl-β-D-glucuronide, a substrate for enzyme β-glucuronidase. The MMO-MUG test utilizes a specific multi-component medium consisting of ammonium sulfate, manganese sulfate, zinc sulfate, magnesium sulfate, sodium chloride, calcium chloride, potassium dihydrogen phosphate, sodium sulfate, anhydrous sodium phosphate, hydrogen sulphide, amphotericin B, ONPG, MUG, and Solanium. Several disadvantages have been recognized and connected with the use of the MMO-MUG test. First, the medium is expensive and currently may be obtained only from one source. It requires a presence of a proprietary dispersing agent Solanium not readily available. Second, the test is approved for estimating of total coliform bacteria as it is recognized that it is not specific enough to distinguish E. coli from other coliforms. Third, it requires the incubation at 35° C. for at least 24 hours which incubation does not allow an addition of indole for specific determination of E. coli since it does not contain tryptophan, the substrate for indole production and since the 35° C. temperature would allow a reaction of temperature sensitive indole positive non-E. coli bacteria if tryptophan were present. At temperatures above 44° C., such reaction does not occur. Furthermore, the test has admittedly a false negative rate of least 13%, and more like 30–40%, since it does not detect MUG-negative E. coli, which error, for lack of better test, was found to be acceptable by the EPA.

In view of the 30–33% E. coli being β-glucuronidase negative, the MMO-MUG test gives false negative results in about 30–34%. Such high false-negative rate of E. coli detection has serious implications for public health. As described in the *Ann. Meeting Amer. Soc. Microbiol.*, Abstracts (1990), when *E. coli* contaminated samples of water from Southern California were examined, about 40% of the samples containing *E. coli* were found to be negative in MMO-MUG test.

The high false negative rate has been confirmed in other studies. A collection of fecal *E. coli* from many parts of the world was examined with both lauryl tryptose (LT) and the MMO-MUG technique, and the 30% false-negative rate was found, as described in the *Journal of Food Protection*, 53: 972 (1990).

Thus, it would be highly advantageous to have available a specific and accurate test which would not depend solely on the determination of MUG-positive *E. coli*.

It is the subject of the current invention to provide such a test. The current method for determination of the contamination by *E. coli* in water, food, seafood or other samples is based on simultaneous measurement of lactose utilization and indole production by *E. coli*. The method is very specific for *E. coli* but allows the determination of the total coliform, fecal coliform and *E. coli*, if desired. In one aspect, method is modified to detect the presence of *E. coli* by using only the indole test.

The indole-producing enzyme tryptophanase was one of the first enzyme tests used for identification of *E. coli*. In the 100 years since Kitasato described the indole test in *Zeitschrift Hyg. Leipzig*, 7: 515 (1889), it has proven to be one of the most useful and definitive tests for *E. coli*. It is used, as described in classical IMViC test published in *Identification of Enterobacteriaceae*, 2nd Ed. Burgess Publ. (1962), for distinguishing *E. coli* from other coliforms.

The major disadvantages of the indole test is that it cannot be combined with tests for lactose utilization because glucose and lactose both inhibit the indole production.

The principle of the indole test is the ability of *E. coli* to form tryptophanase, the enzyme which metabolizes tryptophan into indole. Some genera of the *Enterobacteriaceae* have the ability to produce tryptophanase and accumulate indole at 44.5° C.; other genera do not. For example, *E. coli* produces indole at elevated temperature, but the related fecal coliform, *Klebsiella pneumoniae*, does not. Therefore, the accumulation of indole has proved to be useful and reliable way of distinguishing different members of the *Enterobacteriaceae*.

The formation of tryptophanase is inducible by tryptophan and its analogues. Since a number of species of *Enterobacteriaceae* has ability to produce tryptophanase, the presence of this enzyme results in the accumulation of indole as a catabolite of tryptophan and thus the presence of this enzyme is very useful for identification of *Enterobacteriaceae* bacteria.

The standard medium used for the identification of indole production, described in *Standard Methods for Water and Wastewater Analysis* requires incubation at 35° C. for 24 hours in tryptone water, a carbohydrate-free medium, and testing for indole with Kovacs reagent (*Zeit. Immunitaetforsch. Exp. Ther.*, 55: 311 (1928)). This reaction is based on chromogenic reaction of indole with p-dimethylaminobenzaldehyde. In this test, free indole is removed by extraction to liquid media such as amyl alcohol or xylene to distinguish free indole from residual tryptophan, which also reacts with p-dimethylaminobenzaldehyde under suitable conditions.

An alternative chromogenic reaction for indole, described in *J. Appl. Bacteriol.*, 63: 329 (1987) is based on condensation of indole with glutaconic aldehyde to form red-violet polymethine dyes. While this is a reasonably rapid and sensitive method for determination of indole, the method requires a preparation of tryptophan agar media, lengthy incubation up to 48 hours at 37° C., and the reaction with 1-(4-pyridyl) pyridinium chloride, a not readily available reagent. The later is used to saturate Whatman chromatography paper and needs to be converted to glutaconic aldehyde with sodium hydroxide. After rubbing a loopful of bacteria from a colony, already fully grown on tryptophan agar, on the Whatman paper, the acidification with hydrochloric acid is necessary to develop color reaction. This procedure is lengthy, laborious, requires rare reagents, and thus is not at all suitable for routine multiple-sample use for water testing.

A microtest, based on a similar idea, which is useful for rapid identification of *Enterobacteriaceae* is described in *Acta Path. Microbiol. Immunol. Scand. Sect. B*, 92: 239 (1984). The test utilizes filter disks impregnated with a substrate on which a fully grown bacteria isolate is placed. The disk is reacted with a specific reagent to observe the development of colors characteristic for *Enterobacteriaceae*. Like other clinical diagnostic tests, this one requires a fully grown pure culture of the bacterium to be tested. It is laborious and time-consuming to make such isolates from water samples.

The deficiencies and disadvantages connected with the methods, tests and techniques currently available, as described above, are overcome with the method of the current invention. The current invention is based on the simple observation that tryptophanase, the enzyme responsible for indole production, is strongly repressed in the presence of lactose (*Abstract: Ann. Meet. Amer. Soc. Microbiol.*, Q12 (1990)) and that this repression may be avoided by simply omitting lactose from the medium and replacing it with a suitable synthetic β-D-galactopyranoside substitute such as ONPG (in this application, we use the term "galactoside" and "galactopyranoside" interchangeably). As described above, the ONPG serves to indicate the general ability of a bacterium to utilize lactose. However, unlike lactose, it does not repress tryptophanase or indole production and indole production can be detected by development of the purple color after addition of a suitable reagent such as Kovacs or Ehrlich reagent.

SUMMARY

One aspect of this invention is a sensitive, rapid, specific, accurate and inexpensive method for determination of the presence of total coliform and *E. coli* in water samples, food products and seafood.

Another aspect of this invention is a quick visual method for determination of presence of *E. coli* in water samples, food products and seafood.

Yet another aspect of this invention are the media specifically designed to allow the detection of minute number of *E. coli* in water, in food products and in seafood as well as chlorine and food processing injured *E. coli*.

Still another aspect of this invention is a method for detection of *E. coli* in water samples, food products and seafood utilizing a regular pH medium having the composition which specifically promotes the growth of the weak or injured *E. coli*.

Yet still another aspect of this invention is a method for detection of *E. coli* in water samples, food products and seafood utilizing low pH condition medium.

Yet still another aspect of this invention is a method for detection of *E. coli* in water samples, food products and seafood utilizing low pH condition medium containing trimethylamine-N-oxide.

Yet still another aspect of this invention is a method for detection of E. coli in water samples, food products and seafood utilizing low pH condition medium containing trimethylamine-N-oxide which medium is specifically designed for sole detection of E. coli and does not contain any glucosides or glucuronides.

Still yet another aspect of this invention is a rapid method for detection of E. coli in water, food, and seafood utilizing solely the determination of indole production at incubation of 35° C. followed by incubation at 44.5° C.

Still yet another aspect of this invention is a rapid method for detection of E. coli in water, food, and seafood utilizing solely the determination of indole production at incubation temperature of 35° C. followed by incubation at 44.5° C. utilizing low pH and trimethylamine-N-oxide containing medium.

Another aspect of this invention is the enumeration of E. coli by a membrane filtration method for water samples.

Still another aspect of this invention is the quantification method for determination of a most probable number of E. coli present in water samples, food products, and seafood.

Another aspect of this invention are testing kits for quick visual determination of the presence of E. coli in water, food or seafood, for determination of total coliform and E. coli in water or food samples or in seafood and for enumeration of the number of coliforms and E. coli present in water, food or seafood.

DETAILED DESCRIPTION OF THE INVENTION

Figure 1:
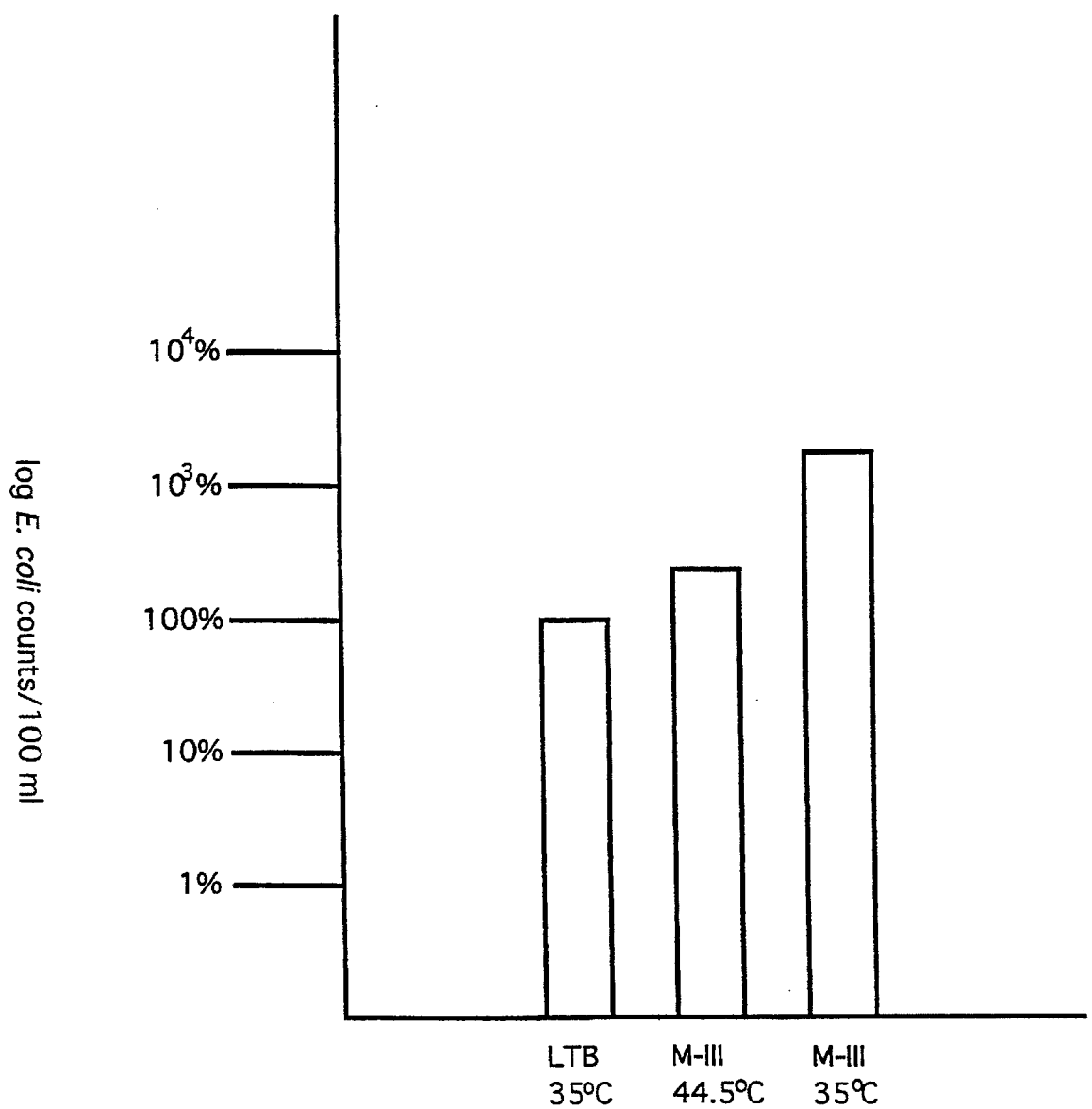
FIG. 1 is a graph comparing a detection of chlorine injured E. coli in standard lauryl tryptose medium and in current medium III.

The current invention is based on finding that E. coli is the only major group of Enterobacteriaceae bacteria which have two most definitive traits typical for their species, namely lactose utilization and indole production at 44.5° C. By combining the method for lactose utilization determination with the method for determination of indole production, or by developing conditions enabling the use of indole test only, a very sensitive, specific, and accurate test for determination of E. coli in water, food, and seafood has been developed.

The test is specific to those Enterobacteriaceae which can simultaneously produce indole and ferment lactose and thus are able to grow and generate color and/or fluorescence in a specific medium containing galactoside and tryptophan as specific substrate for lactose utilization and indole production. In water samples, food products, and in seafood, these Enterobacteriaceae are solely E. coli.

The new method enables detection of the presence of coliform bacteria and E. coli simultaneously in water and food samples. Additionally, the specifically designed medium which promotes the growth of bacteria and provides a substrate for induction of the enzyme tryptophanase allows the detection of minute amounts and even one single E. coli bacteria in chlorinated water, processed food samples, in seafood, etc. The current method further utilizes incubation temperatures to avoid detection of other indole positive but thermolabile bacteria. The method is rapid, accurate and specific and does not require purified, fully grown E. coli culture colonies.

This invention, consequently is based on the observation that E. coli are, under the conditions developed in this invention, able to metabolize lactose and produce indole from tryptophan. The test is rapid, It takes only 24 hours to conclusively determine the presence or absence of E. coli. The test is accurate. It determines with almost 100% accuracy the presence or absence of E. coli in the water or food samples or in seafood without giving false negative or positive readings. The test is sensitive. It can determine the presence of even one E. coli cell and is able to determine the presence of E. coli injured by chlorination or by food processing. The test is quantitative. It utilizes a dilution method to determine a most probable number of contaminating E. coli. The test is specific to E. coli. It is able to distinguish between other coliforms and E. coli.

In one aspect, the method of the current invention simultaneously determines the presence of β-galactoside, an enzyme evidencing lactose utilization, and tryptophanase, an enzyme evidencing a formation of indole.

In another aspect, the method of the current invention provides conditions for specific determination of indole produced by E. coli when E. coli is injured by chlorination or food processing. Using this method, only those bacteria which simultaneously produce indole and utilize lactose give positive results. In water and food samples, such ability is present essentially only in the bacteria E. coli.

The primary difference between the previously disclosed tests, such as MMO-MUG of Edberg, described in Appln. Environm. Microbiol., 54: 1595 (1988), which utilizes two indicators for lactose utilization, namely metabolism of ONPG identified by a presence of yellow color and of MUG identified by fluorescence, the current method uses either of the two, that is either ONPG or MUG as indicator of the presence of lactose utilization and then adds the indole production step, which by producing the red-purple color following the addition of the Kovacs/Ehrlich reagent, confirms unequivocally that the indole formation is present and that the sample contains E. coli.

I. PRINCIPLE OF THE INVENTION

Indole production is generally suppressed by glucose, lactose or by any other readily utilized sugar. Consequently, indole test does not work in the presence of lactose which is known substrate involved in a normal metabolic energy producing pathway of E. coli.

It is well known fact that when E. coli are placed in culture medium containing lactose, an inducible enzyme β-galactosidase is synthesized in large amount. The induced β-galactosidase hydrolyzes lactose (I), according to Reaction Scheme I, to two products, namely to D-glucose (II) and D-galactose (III). These products can be used directly as an energy fuel and a carbon source.

REACTION SCHEME I

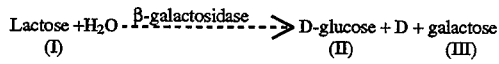

Lactose + $H_2O$ $\xrightarrow{\text{β-galactosidase}}$ D-glucose + D + galactose
(I)                                                        (II)       (III)

This distinct characteristic of E. coli is used as one of the primary features of this invention enabling one to quickly and accurately separate Enterobacteriaceae having this characteristic from those which do not possess it. In the test, the ability to utilize lactose utilization is detected by the hydrolysis of chromogenic or fluorogenic β-D-galactosides.

The second distinct characteristic of E. coli is its ability to utilize tryptophan as carbon or a nitrogen source and to metabolize it with the enzyme tryptophanase. The reaction is detected with the indole test. The basis of the indole test is the reaction illustrated in Reaction Scheme II. Tryptophan (IV) is metabolized with E. coli tryptophanase into free indole (V), pyruvate (VI) and ammonia (VII).

REACTION SCHEME II

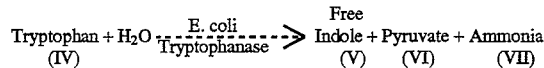

This distinct characteristic of E. coli at 44.5° C. is used as one of the primary features.

Both the first and second distinct characteristics of E. coli are based on metabolic flexibility of E. coli cells. E. coli are chemo-organotrophics, in that they require an organic source of carbon and metabolic energy, however, within this category they are metabolically versatile. As shown in the case of lactose, when there is no glucose present and readily available as an energy and carbon source, E. coli utilize lactose and quickly reorient their enzymatic synthesis to produce enough β-galactosidase, to suffice to metabolize lactose to D-glucose and D-galactose.

Similarly to the lactose, E. coli which normally utilizes ammonia, can also utilize various other sources of nitrogen than ammonia. In fact, when E. coli cells are provided with an ample supply of exogenous amino acid, they stop synthesizing amino acids de novo from ammonia and use the preformed acids instead.

E. coli, can also use certain amino acids as fuel and carbon sources when necessary. The current invention recognizes this propensity of E. coli and advantageously utilizes amino acid tryptophan which contains in its molecule an indole and which can be metabolized by specific tryptophan enzyme tryptophanase to free indole, pyruvate and ammonium. As there are very specific tests known for determination of indole, the current invention utilizes this feature to unequivocally detect bacteria E. coli, which possess both lactose utilization and indole production from all other bacteria which do not possess both these features.

Based on the above background, in practice, the current invention is based on determination of the presence of the enzyme β-galactoside and on the presence of free indole.

As describe above, under these conditions, when ample amount of lactose is present in the medium, the utilization of lactose is catalyzed by and induces the production of the enzyme β-galactosidase, which has distinct chemical properties and can be easily measured or otherwise determined. However, since lactose is known to inhibit production of indole from tryptophan, then clearly, indole cannot be obtained and measured when lactose is present. By substituting lactose with a surrogate compound which is metabolized by β-galactosidase, the inhibitory effect of lactose is removed and indole will form and may be measured simultaneously with the lactose-surrogate's utilization.

This invention further advantageously utilizes the fact that E. coli is such a convertible organism which can respond quickly to all of its metabolic demands. Thus, if the specific lactose-surrogate which can be measured is offered as a sole carbon source and all other more easily utilized carbon sources are eliminated from the media, E. coli will quickly respond by immediate production of β-galactosidase. The E. coli systems for metabolic regulation also recognize tryptophan as a carbon source. Thus, if the tryptophan is offered and all other more easily metabolized carbon sources are either completely eliminated controlled in such a way that they are advantageously utilized in the test, then tryptophanase is formed in large amount by E. coli to be able to convert tryptophan to easily measurable free indole.

II. TESTING CULTURES

In the original laboratory testing of the current invention, three basic bacteriological experimental setups of bacterial cultures were tested. The cultures were fully grown in the laboratory conditions and were chosen to provide an evidence that the current method is able to detect various strains of E. coli including MUG-positive and MUG-negative E. coli and to distinguish between the E. coli, coliform and non-coliform. The experimental setups contained: (1) controls non E. coli non-coliform Enterobacteriaceae; (2) E. coli; and (3) non E. coli coliforms.

Setup 1 (control): Salmonella

Salmonella typhimurium, both lactose and indole-negative.

Setup 2 (experimental): E. coli bacteria

E. coli ATCC 25922, ECOR 13, ECOR 8, ECOR 5, ECOR 4, ECOR 6, ECOR 47, ECOR 13, (obtained from American Type Culture Collection); TC 244, TC 234; TC 218, TC 217, (isolated at University of California, Berkeley); or PF 226, PF 222 (obtained from FDA Laboratory of Peter Feng), both lactose and indole positive.

Setup 3 (experimental): Non-E. coli coliform bacteria

TC 257, Klebsiella Pneumoniae, Enterobacter cloacae, Citrobacter freundii, lactose positive and indole negative.

III. SPECIFIC MEDIA FOR DETECTION OF COLIFORM AND/OR E. COLI

Four basic types of media were prepared with several variations for testing and determination of the best performing media. The basic requirement for the media was that it contains at least an optimal minimum amount of tryptophan or tryptophan-substitute and optimal minimum amount of lactose-surrogate.

The lactose-substitutes were nonfluorogenic compounds such as ONPG, indolyl-β-D-galactoside, X-galactoside (X-GAL) which is 5-bromo, 6-chloro-indolyl-β-D-galactoside, 8-hydroxyquinoline-β-D-galactopyranoside (HQDG), and other known lactose substitutes in amount from 0.01–10 g/l, preferably from 0.05 to 0.5 g per liter of normal solution, or fluorogenic methylumbelliferyl-galactoside (MU-GAL) in amount from 0.01–3.0 g per liter, preferably 0.15 g per liter of concentrated (3×) solution.

A β-glucuronidase substrate may be included for the detection of MUG-positive E. coli. Typical substrates include fluorogenic methylumbelliferyl-β-D-glucuronopyranoside (MUG) or chromogenic p-nitrophenyl-β-glucuronide, 5-bromo-4-chloro-3-indolyl-β-D-glucuronide (X-GLUC), or 8-hydroxyquinoline-β-glucuronide. Each of these substrates can be used in amounts from 0.01–10 g/l, preferably 0.02–0.05 g/l.

The preferred medium contains ONPG or MU-GAL in an amount from 0.01–5g, preferably in amount 0.05–0.10 g per liter.

Optionally, additional inhibitors included in the media are agents such as phenylethyl-β-D-glucoside or sodium fluorocitrate that inhibit those non-*E. coli Enterobacteriaceae* that produce indole at 35° C. If these agents are included, it is possible to use both the β-galactosidase and the indole tests specifically for *E. coli*.

Nonfluorescent chromogenic lactose substitutes are used as a color indicators for the determination of the utilization of lactose or its surrogate. Fluorogenic lactose substitutes produce the fluorescence which is used as an indicator for the utilization of lactose or its surrogate.

Nonfluorescent lactose substitutes normally produce a yellow color (ONPG) or blue color (X-GAL and indolyl-galactosides). Hydroxyquinoline produces intense black pigment in the presence of the ferric salt, such as ferric chloride. Red GAL produces a cherry-red color. MU-GAL produces greenish fluorescence visible under UV.

Indole source typically confers a purple color on *E. coli* containing sample, when the sample is reacted with Kovacs or Ehrlich reagents. In the current medium, tryptophan is a primary indole source. Tryptophan is used as preferred indole source in amount from 0.1 to 20 g/l, preferably 1 g per liter of normal solution and 0.1 to 30 g/l, preferably 3 g per liter of concentrated solution. Indole derived from tryptophan will produce purple-red color. Non-indole tryptophan analogue S-O-nitrophenyl-1-cysteine (SOPC) which gives, when ionized, a bright yellow color, may also be used. O-nitro-thiophenol derived from SOPC produces yellow color but when used in combination with X-galactoside, which produces blue color, the resulting color is green. As illustrated in Table 1 below, the current invention allows medium components variations which result in color variations depending on which combination of the reagents is used.

TABLE 1

Color Indicators - Presence of *E. coli*

| MEDIUM COMPOSITION | LACTOSE UTILIZATION | INDOLE PRODUCTION |
|---|---|---|
| | COLOR INDICATORS | |
| ONPG/TRP | Yellow | Purple |
| X-GAL/TRP | Blue | Dark Purple |
| IndGAL/TRP | Blue | Dark Purple |
| X-GAL/SOPC | Blue | Green |
| ONPG/SOPC | Yellow | Yellow |
| MUG/TRP | Fluorescence | Purple |
| MUG/SOPC | Fluorescence | Yellow |

The medium optionally contains a second nitrogen containing compound such as an ammonium salt, hydrolyzed protein, amino acid mixture, peptide mixture, or yeast extract, preferably tryptose or any other nitrogen containing broth, as an additional source of nitrogen, in amount from 0.05–30 g/l, preferably from 3–30 g per liter of concentrated solution.

Additionally, medium may optionally contain β-galactosidase enzyme inducer such as isopropyl-β-D-thiogalactopyranoside (IPTG), or other enzyme inducers such as methyl-thiogalactoside, or melibiose in amount from 0.01 to 1 g/l, preferably 0.1 g/l of normal medium base and from 0.03 to 3 g/l, preferably 0.3 g per liter of concentrated medium.

To inhibit the growth of interfering bacteria, the medium may optionally also include bacteria growth inhibitors such as sodium lauryl sulfate, bile salt, detergents, surfactants such as tergitol-7, antibiotics such as monensin or nalidixic acid in amount from 0.01 to 1 g/l, preferably 0.1 g per liter of normal medium and from 0.03 to 3 g/l, preferably 0.3 g per liter of concentrated medium.

Additionally, yeast extract may be added in amount from 10 mg-10 g/l, preferably 50 mg/l.

To stimulate resuscitation and growth of injured bacteria, carbohydrates such as glucose, lactose, sorbitol, or glycerol may be added at concentrations that are too low to result in significant repression of trytophanase, typically less than 3 g/l. It could also contain organic buffers such as citrate, HEPES, MES or PIPES.

The above ingredients are dissolved in 1 liter of sterile solution such as distilled deionized water. To the final medium, additional amounts of sodium chloride or any other suitable salt non-toxic to bacteria may be added up to 50 mmol concentration.

Medium typically will also include various inorganic salts in amounts most suitable for performance of the particular function. The medium may be buffered or not buffered. The buffered medium will typically contain any combination of magnesium sulfate, potassium diphosphate, disodium phosphate, sodium lauryl sulfate, or sodium chloride wherein potassium and disodium phosphate performs the buffering function.

The nonbuffered medium will not contain phosphates but will include other salts in any combination and amount.

Typically, the below listed salts, will be added to both buffered and nonbuffered media (1 liter) in amounts:

| magnesium sulfate | 0.01 to 0.5 g/liter |
| sodium lauryl sulfate | 0.01 to 0.5 g/liter |
| monosodium glutamate | 0.05 to 2.5 g/liter |
| ammonium sulfate | 0.02 to 2.5 g/liter |
| sodium chloride | 0.2 to 10 g/liter |
| trimethylamine-N-oxide | 0.1 to 50 g/liter |

The following phosphate salts will be added only to buffered media in amounts per 1 liter of solution.

| potassium diphosphate | 0.05 to 2.5 g/liter |
| disodium phosphate | 0.3 to 15 g/liter |

Salts mixtures such as those used in media I, II, and III, and IV overcome a serious problem in the classic indole test. The classic test, performed in tryptone water, has limited sensitivity at 44.5° C. About a third or a quarter of *E. coli* isolates are unable to produce indole in tryptone water at 44.5° C., even though they can do so at 35° C. Therefore, the British, who use the 44.5° C. indole test, have to reincubate indole-negative cultures at about 35° C. (the Bristish use 37° C.).

The salts included in media I, II, III, and IV, and similar salt mixtures enable virtually every *E. coli* isolate to produce indole from tryptophan at 44.5° C. Therefore, it is not necessary to reincubate indole-negative cultures at 35° C.

Four major types of media were prepared and tested.

The medium I, buffered to pH 6.8–7.4, performs best on water, food or seafood samples containing normal non-injured *E. coli*. The nonbuffered mediums II and III perform very well on weak or chlorine injured *E. coli*, or on *E. coli* injured in food processing. The medium III performs the best on *E. coli* injured by chlorination or by food processing which are present in very small numbers. The medium IV is designed to detect solely *E. coli* and not coliforms.

Medium I and especially medium III are excellent media for detecting total coliforms and MUG-positive *E. coli* at 35° C.

For preparation of all the following media, tryptophan and salts were heat-sterilized and ONPG, IPTG (when used) and MUG were filter-sterilized. The finished medium was always stored in the refrigerator at 2°–8° C. or frozen. The stock solutions was stored in the refrigerator or freezer until used.

A. Medium I—Buffered

Variations (1)–(18) are all buffered and have pH around 6.8–7.4.

(1) Normal Medium I 1 g of tryptophan and disodium phosphate (1–5 g), magnesium sulfate (0.05–0.3 g), potassium diphosphate (0.2–1 g) were dissolved in distilled water. The solution mixture was sterilized at 121° C. for 15 minutes. ONPG was dissolved in distilled water at 5 g/l, filter sterilized at room temperature, and diluted 10-fold with the tryptophan salts solution. The volume was made-up to 1000 ml.

(2) Improved Medium I

The Normal Medium (1) was supplemented with 0.1 g/l of IPTG which was added as a filter-sterilized solution. Solution was gently mixed to achieve dissolution of all components. Until used, the medium was stored in the refrigerator.

(3) Concentrated Medium I

The components of Normal Medium (1) were dissolved in 300 ml to provide three times concentrated medium stock.

(4) Sodium Lauryl Sulfate Medium I 1 g of tryptophan, 0.5 g of ONPG, 0.1 g of sodium lauryl sulfate, 0.1 g of isopropylthio-β-D-galactopyranoside and sodium chloride up to 50 mmol, were mixed with disodium phosphate, potassium diphosphate and magnesium sulfate as described above. The sodium lauryl sulfate was mixed with tryptophan and with other heat-stable ingredients before heat-sterilization.

(5) Tryptose Medium I 1 g of tryptophan, 0.5 g of ONPG, 3 g of tryptose, 0.1 g of sodium lauryl sulfate, 0.1 g of isopropyl-β-D-thiogalactopyranoside and sodium chloride up to 50 mmol, were dissolved in 1000 ml of 0.85% sodium chloride solution.

(6) Buffered Sodium Lauryl Sulfate Medium I 1 g of tryptophan, 0.1 g of magnesium sulfate, 0.5 g of potassium diphosphate, 3 g of disodium phosphate and 0.1 g sodium lauryl sulfate is dissolved in 1000 ml of distilled water. The solution is autoclaved at 121° C. for 15 minutes and 0.5 g of filter sterilized ONPG is added.

(7) Buffered Yeast Medium I 1 g of tryptophan, 0.1 g of magnesium sulfate, 0.5 g of potassium diphosphate, 3 g of disodium phosphate, 0.1 g sodium lauryl sulfate and 50 mg of yeast extract is dissolved in 1000 ml of distilled water. The solution is autoclaved at 121° C. for 15 minutes and 0.5 g of filter sterilized ONPG is added.

(8) Tryptose-Sodium Lauryl Sulfate Medium i 1 g of tryptophan, 0.1 g of magnesium sulfate, 0.5 g of potassium diphosphate, 3 g of disodium phosphate, 0.1 g sodium lauryl sulfate, and 20 g of tryptose is dissolved in 100 ml of distilled water. The solution is autoclaved at 121° C. for 15 minutes and 0.5 g of filter sterilized ONPG is added.

(9) Monosodium Glutamate Medium I 1 g of tryptophan, 0.1 g of magnesium sulfate, 0.5 g of potassium diphosphate, 3 g of disodium phosphate, 0.1 g sodium lauryl sulfate, and 0.5 g of monosodium glutamate is dissolved in 100 ml of distilled water. The solution is autoclaved at 121° C. for 15 minutes and 0.5 g of filter sterilized ONPG is added.

(10) Ammonium sulfate Monosodium Glutamate Medium I 1 g of tryptophan, 0.1 g of magnesium sulfate, 0.5 g of potassium diphosphate, 3 g of disodium phosphate, 0.1 g sodium lauryl sulfate, 0.25 ammonium sulfate, and 0.5 g of monosodium glutamate is dissolved in 1000 ml of distilled water. The solution is autoclaved at 121° C. for 15 minutes and 0.5 g of sterilized ONPG is added.

(11) Sodium Lauryl Sulfate-Ammonium Sulfate Medium I 1 g of tryptophan, 0.1 g of magnesium sulfate, 0.5 g of potassium diphosphate, 3 g of disodium phosphate, 0.1 g sodium lauryl sulfate, and 0.25 ammonium sulfate is dissolved in 1000 ml of distilled water. The solution is autoclaved at 121° C. for 15 minutes and 0.5 g of sterilized ONPG is added.

(12) Buffered Yeast Medium I 1 g of tryptophan, 0.1 g of magnesium sulfate, 0.5 g of potassium diphosphate, 3 g of disodium phosphate, 0.1 g sodium lauryl sulfate, and 100 mg of yeast extract is dissolved in 1000 ml of distilled water. The solution is autoclaved at 121° C. for 15 minutes and 0.5 g of sterilized ONPG is added.

(13) Buffered Yeast Medium I 1 g of tryptophan, 0.1 g of magnesium sulfate, 0.5 g of potassium diphosphate, 3 g of disodium phosphate, 0.1 g sodium lauryl sulfate, and 25 mg of yeast extract is dissolved in 1000 ml of distilled water. The solution is autoclaved at 121° C. for 15 minutes and 0.5 g of sterilized ONPG is added.

(14) Buffered Tryptose Medium I 1 g of tryptophan, 0.1 g of magnesium sulfate, 0.5 g of potassium diphosphate, 3 g of disodium phosphate, 0.1 g sodium lauryl sulfate, and 5 g of tryptose is dissolved in 1000 ml of distilled water. The solution is autoclaved at 121° C. for 15 minutes and 0.5 g of filter sterilized ONPG is added.

(15) Buffered Tryptose Medium I 1 g of tryptophan, 0.1 g of magnesium sulfate, 0.5 g of potassium diacidphosphate, 3 g of disodium phosphate, 0.1 g sodium lauryl sulfate and 2.5 g of tryptose is dissolved in 1000 ml of distilled water. The solution is autoclaved at 121° C. for 15 minutes and 0.5 g of filter sterilized ONPG is added.

(16) Stock Solution Medium I 0.285 g of tryptophan, 0.855 g of disodium phosphate, 0.1425 g of potassium diphosphate, 0.0285 g of sodium lauryl sulfate, 0.0285 of magnesium sulfate, and 0.7125 g of ammonium sulfate is dissolved in 285 ml of saline and used as a stock solution.

(17) Yeast Stock Solution Medium I

To 50 ml of stock solution (16) is added 0.05 g of yeast extract to obtain yeast stock of 1 g/l. The stock solution was diluted 10-fold before use.

(18) ONPG Stock solution—Medium I

To 25 ml of stock solution medium I (16), 0.125 g of ONPG is added. The solution is filter sterilized.

B. Medium II—Nonbuffered

Medium II is low pH, nonbuffered medium.

Medium II is an improved medium I specially suitable for recovery of chlorine injured *E. coli*. This medium is acidified nonbuffered medium having pH around 6.2.

All prior media for detection of coliform and *E. coli* have been poised at pH 6.8–7.4 to buffer against accumulation of acids produced from lactose. Thus, without exception, these media contain buffering compounds, most often buffering salts. All prior art media are buffered. The reason for using buffered media is that color or fluorescence indicators perform optionally under close to neutral pH and since these prior methods depend solely on development of yellow color or fluorescence, the neutral pH is important.

It has been found, however, during the development of this invention, that acidic nonbuffered media poised at pH about 6.0–6.4, preferably at 6.2, give greatly improved recoveries of chlorine injured cells even under the stress, such as the stress imposed during the needed high incubation temperature of 44.5° C. The more acidic media conditions seem to help injured bacteria to maintain a proton gradient across their damaged cell membrane and to help the bacteria to recover.

The new low pH nonbuffered medium utilizes red-galactosidase, obtained from Research Organics, Inc. for detection of coliforms, in amount from 0.05–1 g/liter, tryptophan in amount from 0.1–5 g/liter, and optimally X-GLUC, 5-bromo-4-chloro-3-indolyl-β-D-glucuronide for MUG positive E. coli in amount from 0.01–0.1 g/liter. Optionally, this medium also contains tryptose as the second nitrogen source and other components as described above.

(19) Low pH Nonbuffered Variation Medium II

Medium containing 1 g tryptophan, 0.1 g red galactoside, 0.05 g X-GLUC, and 0.1 sodium lauryl sulfate, 2.5 g ammonium sulfate, and 2.9 sodium chloride was prepared by dissolving the above ingredients in distilled water, pH was adjusted to 6.2 with diluted hydrochloric acid. The medium was filter sterilized.

(20) Low pH E. coli Growth Promoting Medium II

Medium containing 1 g tryptophan, 0.1 g red galactoside, 0.05 g X-GLUC, and 0.1 sodium lauryl sulfate, 2.5 g ammonium sulfate, 2.9 sodium chloride, and 20 g tryptose was prepared by dissolving the above ingredients in distilled water, pH was adjusted to 6.2 with diluted hydrochloric acid. The medium was filter sterilized.

C. Medium III—Nonbuffered—TMAO Containing

Medium III is further improved against Medium II. Medium III is acidic, nonbuffered, and additionally contains trimethylamine-N-oxide. The medium provides a favorable environment for detection of single cell, weak, chlorine or food process injured E. coli. Under the conditions provided by Medium II, E. coli is able to make repairs in its injured cellular membrane due to prior exposure to chlorine or food processing. The medium III contains all components as listed in Medium I and, additionally, it also contains TMAO or other substrate for trimethylamine oxide reductase such as triethylamine oxide or mixed ethyl-methyl amine oxides. E. coli, during the course of the incubation in low pH medium which allows cellular repairs, metabolize neutral TMAO into basic trimethylamine. Trimethylamine raises the pH of the medium during the incubation to pH close to neutral. Increased pH to neutral levels both aids in further growth of E. coli to levels which are easy to detect, and also allows the color or fluorescence indicators ONPG or MUG to be optimally visualized.

The Medium III thus fulfills two functions. First, it provides favorable conditions for weak, chlorine injured or food processing damaged E. coli to make cellular repairs. This is achieved by providing necessary nutrients together with the low pH which help the bacteria to maintain a proton gradient across their damaged cell membranes. Under the low pH, however, the first part of the E. coli detection method is impaired as both ONPG and MUG activity is repressed as well as the growth of E. coli.

The second function of the Medium III is to provide conditions where the E. coli will grow to make them more easily detectable and also to enable the visualization of ONPG and MUG after incubation. The second function is effectively achieved by addition of TMAO and tryptose or any other peptide broth, hydrolyzed protein, peptide or amino acid coctail to the media.

Addition of TMAO is especially useful for detection of E. coli in food products which contain so much carbohydrate that E. coli or other bacteria produce significant quantities of acid which must be neutralized. Since the moderate acidic medium is needed for cellular repair but large amount of acid would further injure the cells, the presence of TMAO assures that the optimal conditions for both the cellular repair growth and test conditions are maintained. The TMAO is metabolized to the base trimethylamine which neutralizes acids and keeps the pH of the incubation mixture during the incubation at a useful range of 6.8–7.4.

The medium III performs very well for both coliform and E. coli even at 35° C. temperature. The medium composition is further improved by eliminating the IPTG and adding the trace of carbohydrates such as glucose, sucrose, etc. to further promote the recovery of the injured cells and growth. The medium III recovers injured cells much more effectively than other standard methods such as lauryl tryptose broth.

(21) Low pH, TMAO containing Medium III

Medium containing 1 g of tryptophan, 0.1 g of ONPG, 0.1 g of IPTG, 0.1 g of sodium lauryl sulfate, 0.05 g of MUG, 2.5 g of ammonium sulfate, 2.9 g of sodium chloride, 0.1 g of magnesium sulfate, and 1 g of TMAO was prepared as above, and filter sterilized. Adjustment of pH to 6.2 was with diluted hydrochloric acid.

(22) Low pH, TMAO and Tryptose containing Medium III

Medium containing 1 g of tryptophan, 0.1 g of ONPG, 0.1 g of IPTG, 0.1 g of sodium lauryl sulfate, 0.05 g of MUG, 2.5 g of ammonium sulfate, 2.9 g of sodium chloride, 20 g tryptose, 0.1 g of magnesium sulfate, and 1 g of TMAO was prepared as above, and filter sterilized. Adjustment of pH to 6.2 was with diluted hydrochloric acid.

D. Medium IV—for Sole Detection of E. Coli

The medium IV is a modified medium III which allows the direct detection of E. coli without intermediate step of detecting the presence of coliform.

The medium is essentially medium III without color or fluorescence indicators needed for the detection of the presence of coliform. The medium IV thus omits ONPG, IPTG, MUG or other glucoside or glucuronide from its composition. The primary source of carbon and nitrogen is tryptophan optionally complemented with tryptose, peptide, hydrolyzed protein, peptone broth, or amino acid coctail. Salt mixture is added to support the growth of the E. coli bacteria. The medium preferably has a low pH between 6.0–6.4, most preferably around pH 6.2. Similarly to above, this pH allows chlorine or food processing bacteria to recover in the low pH milieu. Due to the presence of TMAO, the pH of the medium is raised during the incubation to the normal pH between 6.8–7.4 which allows the purple color development after Kovacs/Ehrlich reagent. The purple color development is characteristic for E. coli.

(23) Low pH, TMAO Containing Medium IV for Sole Detection of E. coli

Medium containing 1 g of tryptophan, 0.1 g of sodium lauryl sulfate, 2.5 g of ammonium sulfate, 2.9 g of sodium chloride, 0.1 g of magnesium sulfate, and 1 g of TMAO was prepared as above, and filter sterilized. Adjustment of pH to 6.2 was with diluted hydrochloric acid.

(24) Low pH, TMAO and Tryptose Medium IV for *E. coli*

Medium containing 1 g of tryptophan, 0.1 g of sodium lauryl sulfate, 2.5 g of ammonium sulfate, 2.9 g of sodium chloride, 20 g tryptose, 0.1 g of magnesium sulfate, and 1 g of TMAO was prepared as above, and filter sterilized. Adjustment of pH to 6.2 was by hydrochloric acid.

Basic medium I, II, III, and IV is typically prepared as a stock solutions and used for preparation of many specific solutions listed in its group.

The above detailed 24 media and other variations commensurate with the basic composition of the media, based on the above-listed ingredients, or other substitute ingredients which satisfactorily substitute one or more of ingredients above listed, are contemplated to be within the scope of this invention.

Medium solutions are sterilized either by autoclaving, by micropore filtration, irradiation or by any other method suitable for such purposes, as long as such a method does not damage or remove individual ingredients. The sterilization can be achieved by using sterile glassware, solution and ingredients. Alternatively, partial mix may be autoclaved, or complete medium may be sterilized by filtration.

The stock solutions or ready made solutions are preferably stored at 2°–8° C. in the refrigerator or they may be freeze-dried, frozen, dry-blended and irradiated, vacuum dried, lyophilized or preserved in any other suitable manner recognized in the industry.

The ingredients of any medium or similar medium may also be mixed as a dry mixture or in any suitable volatile organic or inorganic solvent. Sterilization may be achieved by irradiation or by the solvent itself.

IV. Methods for *E. coli* Detection-Conditions

The conditions such as the incubation temperature, the incubation time, the most suitable medium, pH, etc., developed and determined to be optimal for the detection of coliform and/or *E. coli* in water samples, food products and seafood were tested in several studies.

Ultimately, the incubation temperature and time was found to be optimal at 2–6 hours, preferably 4 hours of initial incubation at 35° C. followed by 16–24 hours, preferably 20 hours incubation at 44.5° C. The sole incubation at 44.5° C. for hours is suitable for detection of *E. coli* with Medium IV.

Most suitable media for detection of *E. coli* were found to be Medium III and IV. The Medium III is most suitable for tests where both coliform and *E. coli* are intended to be detected. Medium IV is preferable when only *E. coli* are intended to be detected. Both these media III and IV are most useful for detection of small number, even one *E. coli*, and those which are weak and injured.

Medium having low pH, such as between pH 6.0–6.4, preferably 6.2 was found to be the most suitable for detection of injured or weak *E. coli* present in small numbers.

Addition of trimethylamine-N-oxide to the low pH medium improved the recovery of injured *E. coli* cells and was most useful for detection of *E. coli* in chlorinated drinking water, in heavily treated effluent water, in food products previously processed whether physically, chemically or mechanically and in the seafood in which the *E. coli* may be significantly injured and weakened but not killed.

When used for bacteriological testing for presence of *E. coli*, an appropriate amount of the sterile medium is mixed with a water sample to be tested in amount from 1:10 to 10:1 ratio, preferably 2:1 ratio, of water sample to medium. For food samples, the food sample is added to a medium in proportions 1:10 of sample to medium. The solution is gently swirled or mixed and incubated at temperatures from 30°–50° C., preferably around 35°–36° C., followed by 18–22 hours at 44.5° C. With prior art media used before this invention, it was recognized that the direct incubation of *E. coli* samples at higher temperatures of around 44.5° C. leads to false negative results because at that temperature, weak or injured *E. coli* will not survive.

The ability to incubate the mixture containing *E. coli* at higher temperatures and utilizing indole test is an additional improvement introduced in this invention.

In prior art tests, the temperature was limited to temperature around 35° C. At this temperature, some indole positive but thermolabile non-*E. coli* may interfere with *E. coli* test. At 44.5° C. incubation, no other bacteria than healthy *E. coli* closely related fecal coliforms (thermotolerant coliforms) survive. However, in the medium of the current invention, which is bacteria growth promoting and which allows low pH condition conducive to the repair of the cellular membrane injured by chlorination or by food processing, even injured *E. coli* are detected.

Moreover, it is possible, using the current invention to solely utilize the higher temperatures of 44.5° C. The medium III provides such a sensitive milieu for growth and repair of *E. coli* that these *E. coli* are able to be detected at such high temperature.

V. Methods for *E. coli* Detection

There are two basic methods for detection of *E. coli*. One method detects both fecal coliform and *E. coli*. The second method detects solely *E. coli*. Difference between the two methods is in the medium used for the method and the conditions under which the detection is performed.

Generally, in both methods, the samples are incubated for 24 to 48 hours, preferably for 4 hours at 35° C. and 20 hours at 44.5° C. Typically, if there is no color developed at 24, the incubation can be extended to 48 hours. However, 24 hours is usually sufficient to conclusively detect the presence of *E. coli* or determine their absence. If there is no yellow or purple color visible in the sample then there is no *E. coli* present. Normally, yellow color which indicates the presence of a fecal coliform such as *E. coli* will be determinable at 15–18 hours, latest at 24 hours, after which the Kovacs or Ehrlich reagent is added for specific *E. coli* identification.

When the water or food sample is contaminated with a small number of *E. coli* or when the *E. coli* are weak or injured, the color development takes longer but typically no longer than 24 hours. On the other hand, a water or food samples contaminated with large numbers of coliforms or *E. coli* develop the color in the medium fairly soon and positive results may be obtained as soon as around 2–6 hours.

Typically, the current method for determination of coliform and *E. coli* will utilize any media I–III variations (1)–(22). The sample to be tested, that is water, food or seafood or the water in which the seafood or the water in which the seafood is kept is added to the medium. The mixture of medium and water is incubated at 35° C. for around 4 hours, then the temperature of incubation bath is raised to 44.5° C. or the mixture is moved to a 44.5° C. incubator or both and the sample is further incubated. The development of the yellow color can be followed during the incubation. Typically, when the yellow color develops, it is concluded that the fecal coliforms are present and detectable and the Kovacs or Ehrlich reagent is added. If the purple color appears, *E. coli* are present. Alternatively, medium III can be used solely at 35° C. temperature for 24 hours for detection of total coliforms and *E. coli*.

The method for sole detection of *E. coli* utilizes medium IV, variation (23) or (24). Variation (24) is preferred because it provides tryptose as a carbon source and, in this way, it promotes the growth of *E. coli*. At 44.5° C. temperature, no other indole producing bacteria will be detected and therefore, the method is very specific for *E. coli* only.

In this method, the sample is mixed with the medium IV in the same fashion as above and incubated at 35° C. for 4 hours, followed by incubation at 44.5° C. for 20–24 hours. Then the Kovacs or Ehrlich reagent (2–5 drops) is added and the development of the purple color is followed. If one wants to detect indole earlier or if one wants to incubate the test medium longer, it is important to remember that the indole reagents are toxic to the bacteria. Therefore, one must remove a small amount (0.2–0.5 ml) of the culture for indole testing. If there is no purple color, there is no *E. coli* contamination.

In alternative, it is possible to incubate the sample solely at 44.5° C. for as long as it takes to observe the presence of the purple color but no longer than 48 hours. Typically, if there is *E. coli* contamination, it is observed at around 14–24 hours, but no later.

Membrane Filter Technique (MFT)

The principles of this invention is equally useful with membrane filter techniques previously described for detection of fecal coliforms and *E. coli*. For membrane filter technique, 100 ml portion of water sample is filtered through a suitable microporous filter (such as 0.45 µm pore diameter Gelman GN6 or Millipore HA or GS) that captures bacteria from the sample. Then the filter is transferred aseptically to a petri dish containing a filter paper pad saturated with a suitable medium. The suitable medium is any of the medium I–IV as described for the multiple fermentation tube (MPN) techniques. The following variations of the media are suitable for MFT. The protein hydrolysate (tryptose) concentration is increased to 2%. This enables bacteria to form larger colonies. A substrate such as X-GLUC that forms an insoluble product that will be localized to the bacterial colony is used for the β-glucuronidase test. After a suitable incubation (for example 4 hours at 35° C. followed by 20–24 hours at 44 5° C.), the filter is transferred to a paper pad saturated with the indole reagent used in standard spot tests for indole; acidified p-dimethylaminocinnamaldehyde.

In such a test, *E. coli* colonies appear to be greenish or bluish, either because of their indole production or their β-glucuronidase activity or both traits. Other fecal coliforms do not have the dark bluish or greenish color. They will simply have the characteristic of whatever β-galactoside was used. For example, if RED-GAL is used, they are red; if MU-GAL is used, fecal coliforms fluoresce. Therefore, by inspecting a filter under a dissecting microscope, it is very easy to distinguish and enumerate *E. coli* and other fecal coliforms recovered from the water sample.

VI. TESTING OF THE METHODS

Media and the method of the current invention were tested in series of experiments including laboratory isolates samples in water and actual samples of water obtained from river, well, effluent, etc., using different media and test conditions.

Testing of Laboratory Isolates

The first study concerned medium I used for detection of total coliform and *E. coli* (laboratory isolates) in water samples. Water samples containing *E. coli*, other coliforms, or bacteria such as salmonella were prepared in the laboratory and tested using the medium I, variation 1.

The current test was run on four strains of *E. coli*, namely *E. coli* strain ATCC 25922-tubes 1 and 2, ECOR 4-tubes 3 and 4, ECOR 5-tubes 5 and 6, ECOR 6-tubes 7 and 8. Each tube containing 3 ml of medium I was inoculated with approximately 1000 *E. coli* cells in saline.

All tubes were incubated for 18 hours at 35° C. after mixing the water sample containing *E. coli* with the medium I variation number 3. After 4 hours, the yellow color development was observed in aqueous, lower phase in tubes 1–8, This indicated β-galactosidase activity and the presence of coliform in all tubes. After addition of 2 drops of Kovacs' reagent to tubes 2, 4, 6, and 8, reddish-purple ring on the top of the solution in tubes 2, 4, 6 and 8 showed the presence of indole. Indole production then indicated the presence of indole-positive fecal coliforms. In water, most indole positive fecal coliforms are *E. coli*. Both coliforms and *E. coli* are easily and quickly determined when medium I and method of this invention is used.

In comparison, the non-*E. coli* coliform samples in tubes 9–14 illustrate the method using non-*E. coli* coliform and non-coliform bacteria present in water samples. Specifically, in tubes 9 and 10 coliforms are *Enterobacter cloacae* (1000 cells), in tubes 11 and 12 coliforms are *Citrobacter fruendi* (1000 cells), and in tubes 13 and 14 coliforms are *Klebsiella pneumoniae* (1000 cells). In tubes 15 and 16 are noncoliform *Salmonella*. All these bacteria are indole negative. When submitted to the same testing procedure as described above, the yellow color was seen in all tubes 9–14. When the Kovacs reagent was added to tubes 10, 12 and 14, there was no color change indicating the absence of *E. coli*. The presence of the yellow color and the absence of the purple color indicated the absence of the indole formation, showing that there were no indole-positive bacteria present and that all bacteria present in tubes 9–14 were indole-negative, i.e., they were coliform but not *E. coli*.

As a control for testing the accuracy of both coliform and *E. coli* test, non-coliform bacteria *Salmonella* was tested using the same procedure. The same number, that is around 1000 salmonella cells were inoculated into medium I, variation 1. The mixture was incubated, as above, and Kovacs reagent was added. The liquid in tubes 15 and 16, as can be seen, remained colorless, and did not show either the yellow color for coliform, nor the red-purple color for *E. coli*. *Salmonella* bacteria were thus shown not to possess lactose utilization and indole formation.

The results given by the tests using the medium I containing tryptophan and ONPG can be summarized as follows.

Colorless result in both aqueous and organic phases indicates the absence of both *E. coli* and coliform.

Yellow color in the aqueous phase indicates the presence of coliform which may or may not include *E. coli*.

Yellow color in the organic phase following the reaction with the Kovacs reagent indicates the absence of *E. coli*.

Red-purple color in the organic phase following the reaction with the Kovacs and the presence of yellow color in the aqueous phase reagent indicates the presence of *E. coli*.

In the medium variation, as discussed above if the X-GAL is exchanged for ONPG, then instead of the yellow color, the blue color is obtained indicating the presence of coliform.

In the medium variation containing MU-GAL instead of ONPG, the samples containing coliform have blue fluorescence under UV light.

In the medium variation containing HQDG in the presence of ferric chloride, the presence of coliform is indicated by black pigment.

In the medium where the X-GAL is used, instead of ONPG and SOPC is used instead of tryptophan, the green color evidences the presence of E. coli. SOPC produces yellow color, X-GAL produces blue color. Combined, they produce the green color indicating the presence of E. coli.

The E. coli, as described above, test is also useful for enumeration of the number of present E. coli. Typically, the serial dilution of the water sample in saline or in 0.1% peptone, of the water sample is made, as described in Example 5, and then the test is run as described above. The presence of the yellow and purple color is recorded in all dilutions. Results are calculated using the Most Probable Numbers table, according to methods known and accepted in the art.

Testing of Environmental Water Samples

The second study for testing of medium I was done on actual surface and ground water samples. New medium I, variation 1, containing ONPG, MUG, and tryptophan was used. Results were compared to E. coli medium for fecal coliform which utilizes LTB medium containing 20 g of tryptose, 5 g of lactose, 2.75 g of dipotassium hydrogen phosphate, 2.75 g of potassium dihydrogen phosphate, 5 g sodium chloride and 0.1 g of sodium lauryl sulfate dissolved in distilled water, in the first step and EC medium which is essentially the same but contains a mixture of a bile salts (1.5 g) in place of sodium lauryl sulfate. Incubation was run at 35° C. for 24 hours to 48 hours for LTB and for additional 24 hours at 44.5° C. for EC medium.

Results are given in Table 2. Results show clearly that even at temperature 35° C. the results obtained by the current method are comparable to the standard fecal coliform test. In instances where the results were not comparable, there were some reasons for it.

than those found by the standard E. coli fecal coliform test. That points toward higher sensitivity of the current invention.

To determine the relative sensitivity of the medium and method of the current invention and to compare it to the MMO-MUG (Colilert) test and to the standard EC-MUG currently utilized for determination of contamination of water samples with E. coli, sample through both tests at 35° C. incubation temperature. Results are shown in Table 3.

TABLE 3

| | Comparison of Fecal Coliform, Current and MMO-MUG Tests (35° C.) | | | |
|---|---|---|---|---|
| | FECAL | INDICATOR | | |
| MEDIUM | COLIFORM | ONPG | MUG | INDOLE |
| Standard EC | 800 | | | |
| Current | | 2400 | 1300 | 5000 |
| MMO-MUG | | 1300 | 300 | |

Sample was a surface water. Data are 5-tube MPN (#/100 ml)

Standard E. coli method utilized lauryl tryptose medium as described above, MMO-MUG method as described below and medium I under the conditions of the current method, using the incubation at temperature 35 C.

The results show that both MMO-MUG and the current test (medium of the current invention) resulted in much higher numbers of E. coli detected than by the standard EC method, with the detection by the current method of almost twice as many as E. coli in the water sample than MMO-MUG even at temperature 35° C. The explanation and one reason for observed discrepancies and for higher sensitivity of the current method are the components and amounts of various components in the current medium I which promotes the E. coli growth. MMO-MUG medium does not and is not able to do that. The second reason for discrepancies

TABLE 2

| | | Comparison on TAG with the Standard Fecal Coliform Test on Surface and Groundwater | | | |
|---|---|---|---|---|---|
| | WATER | EC MEDIUM | TAG MEDIUM | | |
| NO | SAMPLE | FECAL COLIFORM | ONPG | MUG | INDOLE |
| 1 | Surface | 500 | 300 | 170[a] | 300 |
| 2 | Surface | 2800 | 5000 | 5000 | 5000 |
| 3 | Surface | 1300 | 3000 | 3000 | 3000 |
| 4 | Surface | 800 | 800 | 800 | 800 |
| 5 | Surface | 110 | 800 | 220 | 800[c] |
| 6 | Surface | 330 | 300 | 300 | 300 |
| 7 | Ground | <2 | <2 | <2 | <2 |
| 8 | Ground | 5000 | 24,000 | 2700[d] | 24,000 |

5-Tube MPN (#/100 ml)

In samples 3, 4, and 6, both tests resulted in the same number of E. coli and both ONPG, MUG, and indole tests detected the same number of E. coli in these samples. In sample 1 and 5, where the ONPG and indole tests gave much larger numbers than those found by MUG, it has been subsequently found that there was a substantial number of MUG-negative E. coli present in these samples. In some samples, (2, 3, 5, and 8), the values found by the medium containing either ONPG or MUG and indole, were higher observed between the two tests was that, in this particular sample, there was a large number of MUG-negative E. coli, which the MMO-MUG medium is not able to detect.

Nevertheless, regardless whether the ONPG and MUG were used, the current method is much more sensitive than MMO-MUG method. The difference in sensitivity of the current version against MMO-MUG test is significant at the 95% level.

Subsequently, in another set of studies, it has been found that at 35° C. temperature, the indole test may detect some non-thermotolerant indole positive non-E. coli bacteria and in this way to give false positive results. The results obtained in these studies are summarized in Tables 4–9.

Testing—Water Samples of Various Environmental Origins

To test the utility of the current invention in field, water samples of various environmental origin were collected and submitted to testing using the methods of the current invention.

The tests methodology for this study is outlined below. The tests were performed on four different types of water: well water, river water, groundwater, and effluent water. Three types of water tests were run in parallel: (1) Standard Methods which utilizes lauryl tryptose broth, brilliant green lactose broth, and/or EC medium for determination of total coliform (TC) and fecal coliform (FC). The findings were expressed in most probable number (MPN) according to Multiple-Tube Fermentation Technique #9221 published in *Standard Methods for the Examination of Water and Wastewater*, 17th Edition, Publ. American Public Health Association, Washington, D.C. (1989); (2) MMO-MUG Test; and (3) the current test. All tests were run at 35° C. and the current test was run at 35° and 44.5° C. Findings from these tests were confirmed by bacterial identification on bacterial plates. All media for EC and MMO-MUG were purchased from commercial sources. All ingredients for preparation of the current medium I were similarly purchased from commercial sources, but the medium I was prepared in-house according to the formulation described above.

The water samples were the well water, river water, groundwater, and chlorinated secondary sewage effluent. These samples were collected in sterile containers according to standard method used in the industry. Each sample was analyzed with the five-tube multiple fermentation tube assay to obtain a most probable number (MPN) estimate of bacterial density in the sample. In this test, 10 ml portions of water sample were added to each of five culture test tubes that already contained 10 ml of double-strength of tested medium I, variation (I). This resulted in set of five tubes, each containing a mixture of water samples and medium ingredients in a total volume of 20 ml per tube. The final concentration of medium ingredients in each tube was that of single strength medium.

The five-tube multiple fermentation tube (or 5 tube MPN) test is most accurate if one has both positive and negative tubes among the set of five tubes. To achieve this with concentrated samples (i.e., containing large number of *E. coli*) it is necessary to dilute some samples. Thus some samples were diluted with sterile buffer to get a volume of 10 ml that was added to 10 ml of double-strength medium. For example, in Table 4, run #2, 0.1 ml of river water was used and 9.9 ml of sterile medium I in each of the 5 MPN tubes. In runs #3 and #12, 1.0 ml portions of river water samples, respectively, and 9.0 ml sterile medium I in the various MPN tubes were used.

The total coliform count (TC) was obtained in two steps: the presumptive coliform count and the confirmed coliform count. For the presumptive count, water samples were mixed with lauryl tryptose broth and incubated at 35° C. Tubes that supported gas production in 24 or 48 hours were scored as positive. For the confirmed coliform count, each positive tube as well as each tube that supported heavy bacterial growth in the presumptive test was used to inoculate a fresh tube of brilliant green lactose broth. Each tube of brilliant green lactose broth that supported gas production after 24 or 48 hours incubation at 35° C. was scored as positive in the confirmed coliform test. The pattern of positive tubes was identified and the Most Probable Number Table was used to obtain a most probable number (MPN) estimate of the confirmed coliform population, The MPN values obtained in the confirmed coliform test were recorded as total coliform (TC). The data are presented in Table 4 as total coliform bacteria per 100 ml of water sample.

As seen from the results, well water and groundwater (#1 and 4) contained no total coliform (TC) in column 1; river samples (#2, 3, 5, 8, 10, 12 and 13) contained from 2.2 to more than 160 coliforms per 100 ml; and sewage effluent water (#6, 7, 9, 11, 14–16) contained from less than 2.2 to more than 16 coliforms per 100 ml. Samples #1, 4 and 7, contained fewer than 2.2 coliforms/100 ml.

In the second column, results for presence of fecal coliform (FC) are seen. FC are thermotolerant coliforms; they can grow and produce gas from lactose even at an elevated temperature of 44.5° C. A fecal coliform count was made by manipulation of the fermentation tubes that were used for the total coliform count. Each lauryl tryptose broth (presumptive coliform) tube that supported gas production or abundant bacterial growth by 24 or 48 hours was subcultured in 10 ml of EC broth and incubated for 24 hours at 44.5° C. Presumptive coliform tubes that showed no gas production were presumed to be devoid of fecal coliforms and were not subcultured. After 24 hours at the elevated temperature, each EC tube showing gas production was scored as FC positive. Then the MPN table was used to obtain an MPN for fecal coliforms. As expected, the FC was less than TC in many cases.

TABLE 4

| # | SAMPLE-WATER | ml | MPN TC 35° C. 1 | MPN FC 35° C. 2 | MMO-MUG ONPG 35° C. COLIFORM 3 | MMO-MUG MUG 35° C. E. COLI 4 | CURRENT ONPG 35° C. COLIFORM 5 | CURRENT IND 44.5° C. E. COLI 6 |
|---|---|---|---|---|---|---|---|---|
| 1 | Well | 10 | <2.2 | <2.2 | <2.2 | <2.2 | <2.2 | <2. |
| 2 | River | 0.1 | 220 | 220 | <220 | <220 | 1600+ | <220 |
| 3 | River | 1.0 | 160+ | 160+ | 160 | 22 | 160+ | 22 |
| 4 | Ground | 10 | <2.2 | <2.2 | <2.2 | <2.2 | <2.2 | <2.2 |
| 5 | River | 10 | 16+ | 2.2 | 16+ | <2.2 | 16 | <2.2 |
| 6 | Effluent | 0.001 | 160,000+ | 160,000+ | 160,000+ | 160,000+ | 160,000+ | 160,000+ |
| 7 | Effluent | 1.0 | <22 | <22 | <22 | <2.2 | <22 | <2.2 |
| 8 | River | 1.0 | 22 | <22 | 160+ | 2.2 | 160+ | 2.2 |
| 9 | Effluent | 1.0 | 160+ | 22 | 160+ | 22 | 160+ | 22 |
| 10 | River | 10 | 16+ | 9.2 | 16+ | 9.2 | 16+ | 9.2 |
| 11 | Effluent | 10 | 9.2 | 2.2 | 16+ | 2.2 | 16+ | 5.1 |

TABLE 4-continued

| SAMPLE-# | WATER | ml | MPN TC 35° C. 1 | MPN FC 35° C. 2 | MMO-MUG ONPG 35° C. COLIFORM 3 | MMO-MUG MUG 35° C. E. COLI 4 | CURRENT ONPG 35° C. COLIFORM 5 | CURRENT IND 44.5° C. E. COLI 6 |
|---|---|---|---|---|---|---|---|---|
| 12 | River | 1 | 51 | <2.2 | 160+ | <2.2 | 160+ | <2.2 |
| 13 | River | 10 | 16 | <2.2 | 16+ | <2.2 | 16+ | <2.2 |
| 14 | Effluent | 0.1 | 1600+ | 1600+ | 1600+ | 920 | 1600+ | 1600 |
| 15 | Effluent | 1 | 160+ | 160+ | 160+ | 160+ | 160+ | 160+ |
| 16 | Effluent | 10 | 16+ | 16+ | 16+ | 16+ | 16+ | 16+ |

W = Well water
R = River water
G = Groundwater
E = Effluent water
TC = Total Coliform
FC = Fecal Coliform
ONPG = o-nitro-β-galactopyranoside
MUG = 4-methylumbelliferyl-β-D-glucuronide
IND = Indole
MPN = Most Probable Number In column 3, which summarizes coliform detected by MMO-MUG test, MMO-MUG medium was inoculated with water sample and incubated for 24 hours at 35° C. Any tube that turned yellow was scored positive for ONPG, that is for lactose utilization based on the metabolism of a lactose analogue for the total coliform count. These yellow tubes were then scored to obtain a MPN for the ONPG version of the total coliform count. As seen from column 3, in many cases, the MMO-MUG ONPG agrees with the total coliform (TC) test as well as might be expected, given the statistical uncertainty of the MPN test. However, for two runs, #8 and #12, the TC values lie below the 95% confidence intervals of the MPNs calculated from the MMO-MUG ONPG tubes.

In column 4, which summarizes E. coli detected by the MMO-MUG, the E. coli MMO-MUG test was performed, by examining the same MMO-MUG tubes as in column 3 for the presence of fluorescence under UV irradiation in a darkened room. Fluorescent tubes were scored MUG-positive and presumably E. coli positive. The obtained data were used to calculate the MUG MPN's shown in Table 4, column 4. As seen from column 4, in runs #1, 2, 4, 7 in which the ONPG test was negative, there was no fluorescence observed and it was thus concluded that there was no E. coli present. In runs #3, 5, 8, 9, 11, 12, 13, and 14, where the ONPG test indicated high counts of coliforms, less than half of the ONPG (Coliform) positive tubes fluoresced, indicating that most of the coliforms in those samples were not E. coli.

In columns 5 and 6, which summarize detection of the coliform by ONPG and E. coli by indole, medium I was used at 35° C. (column 5) or, in alternative for 4 hours at 35° C., followed by 20 hours at 44.5° C. (column 6) to test the ability of the ONPG and indole (IND) portions of the current test to detect total coliforms (ONPG) and E. coli (IND). After 24 hours incubation at 35° C., tubes were examined, yellow tubes were counted and the MPN for ONPG was obtained. These MPN values are given in Table 4, column 5. Column 5 shows that the results obtained with the ONPG tests in the MMO-MUG and the current medium I were almost identical in 15 of the 16 runs. However, in run 2, the current ONPG test proved to be much more sensitive than the MMO-MUG ONPG test.

Based on the finding that at 35° C. the indole test seems not to be as specific for E. coli as desirable as some non-E. coli coliforms produce indole at 35° C., the current test was changed to incubate the samples at 35° C. for 4 hours and at 44.5° C. for 20 hours. At 44.5° C., these coliforms do not survive higher temperatures, particularly the temperature above 41° C. The specificity of indole test for detection of E. coli increases substantially when the test is performed above 41° C. temperature. Therefore, the current test was performed at 44.5° C., as seen in column 6, providing both fecal coliform and specific E. coli results. After cultured tubes were inoculated with water samples, they were incubated at 35° C. for 4 hours to enable bacteria to start growing. Then, they were shifted to 44.5° C. and incubated for additional 20 hours. After the incubation, tubes were scored for ONPG at 44.5° C. and for indole production by E. coli. The MPN for the 44.5° C. indole production are given in Table 4, column 6. In all but two cases, E. coli MPNs obtained from the MMO-MUG test agreed well with those obtained by the current indole test, indicating equivalence of the methods, within the limited number of water samples and the statistical uncertainty inherent in the MPN test.

Bacteria in several positive-rated tubes were identified by further bacteriological analysis. During this analysis, a small portion of liquid from a positive tube was removed and streaked onto MacConkey lactose agar in order to obtain isolated colonies and confirm lactose fermentation—lactose positive. Colonies were transferred and restreaked on fresh blood agar medium to obtain purified colonies of bacteria which were then identified to the species level by use of Microscan-Auto-Scan-Walk/Way machine. In this evaluation, many tubes contained more than one species of bacteria. However, the current method was efficient in the determination of the presence or absence of E. coli in the water samples and the results of samples 3 and 8 confirmed that there were E. coli present.

Comparative study was then done between MMO-MUG at 35° C. and medium I at 44.5° C. The detection of coliform and E. coli was confirmed bacteriologically. The results are summarized in Table 5.

TABLE 5

Effect of Incubation Temperature on *E. coli* Detection

| TEST | WATER SAMPLE | MEDIUM | INCUBATION TEMPERATURE | TIME | ONPG | INDOLE | BACTERIOLOGY |
|---|---|---|---|---|---|---|---|
| 1 | River (5) | I | 44.5° C. | 24 hours | + | + | *E. coli* |
| 2 | Effluent (5) | I | 35° C. | 24 hours | + | + | Coliform *Vibrio fluvialis* *Hafnia alvei* |
| 3 | River (5) | I | 35° C. | 24 hours | + | + | Coliform *Aeromonas* *Serratia fonticola* |
| 4 | Effluent (5) | I | 35° C. | 24 hours | + | – | Non-coliform *Klebsiella Pneumoniae* *Serratia Odorif* |

All samples 1–4 were tested separately both for indole presence and bacteriologically. Only at 44.5° C., the current indole test was specific for *E. coli*, as bacteriologically confirmed in the tested river water samples (1). The same experiment performed on effluent and river water samples (2 and 3) at 35° C., picked-up other indole positive coliform (?) bacteria. Indole test of the current invention was more specific for *E. coli* at 44.5° C. than at 35° C.

In another series of experiments performed, it was found that an indole test is additionally able to detect MUG-negative *E. coli* which the tests not containing indole, such as MMO-MUG, are unable to detect. Thus, the MMO-MUG test results in false negative results in case where there is MUG-negative *E. coli* present. The current method at 44.5° C. is also able to distinguish between *E. coli* and other fecal (thermotolerant) coliforms. Therefore, the current method is more specific than the classic fecal coliform test and than the MMO-MUG test.

In order to determine how serious the inability of MMO-MUG to recognize MUG-negative *E. coli* is, 90 separate *E. coli* isolates were obtained from environmental waters (Table 6).

Environmental water samples containing mild stains of *E. coli* were collected from rivers, wells from chlorine treated effluents, ponds, creeks, dugouts, beaches, lakes, etc. Samples were either pristine, nontreated, or chlorine treated. The MMO-MUG and current method including indole test were used for detection of *E. coli*, and for the formation of gas. Results are summarized in Table 6.

TABLE 6

(*E. Coli* - Environmental Sources)

| | SOURCE | MUG | INDOLE | GAS |
|---|---|---|---|---|
| 1 | River | – | + | + |
| 2 | River | +++ | + | + |
| 3 | Effluent* | +++ | + | + |
| 4 | Effluent* | +++ | + | + |
| 5 | River | +++ | + | + |
| 6 | River | ++ | + | + |
| 7 | Well | +++ | + | + |
| 8 | River | +++ | + | + |
| 9 | River | ++ | + | + |
| 10 | River | – | + | + |
| 11 | River | +++ | + | + |
| 12 | River | +++ | + | + |
| 13 | River | +++ | + | + |

TABLE 6-continued

(*E. Coli* - Environmental Sources)

| | SOURCE | MUG | INDOLE | GAS |
|---|---|---|---|---|
| 14 | Effluent* | ++ | + | + |
| 15 | Effluent* | +++ | + | + |
| 16 | River | + | + | + |
| 17 | River | +++ | + | + |
| 18 | River | +++ | + | + |
| 19 | River | – | + | + |
| 20 | River | +++ | + | + |
| 21 | River | +++ | + | + |
| 22 | River | +++ | + | + |
| 23 | River | ++ | + | + |
| 24 | Pond | + | + | + |
| 25 | River | +++ | + | + |
| 26 | Mun. D/W | ++ | + | + |
| 27 | Effluent* | +++ | + | + |
| 28 | Effluent* | + | + | + |
| 29 | Well*** | +++ | + | + |
| 30 | River | + | + | + |
| 31 | River | +++ | + | + |
| 32 | River | +++ | + | + |
| 33 | River | ++ | + | + |
| 34 | River | – | + | + |
| 35 | River | +++ | + | + |
| 36 | River | ++ | + | + |
| 37 | River | +++ | + | + |
| 38 | Well | ++ | + | + |
| 39 | Well | ++ | + | + |
| 40 | Well | +++ | + | + |
| 41 | Well | ++ | + | + |
| 42 | River | +++ | + | + |
| 43 | River | +++ | + | + |
| 44 | River | ++ | + | + |
| 45 | River | – | + | + |
| 46 | River | + | + | + |
| 47 | River | +++ | – | + |
| 48 | River | – | + | + |
| 49 | River | +++ | + | + |
| 50 | River | +++ | + | + |
| 51 | River | – | + | + |
| 52 | Cooling pond | – | + | + |
| 53 | Effluent** | +++ | + | + |
| 54 | River | – | + | + |
| 55 | Well | +++ | + | – |
| 56 | Well | + | + | + |
| 57 | Effluent* | + | + | + |
| 58 | Effluent* | + | + | + |
| 59 | River | ++ | + | + |
| 60 | Beach | – | + | + |
| 61 | Beach | + | + | + |
| 62 | Beach | – | + | + |
| 63 | Beach | +++ | + | + |

TABLE 6-continued (E. Coli - Environmental Sources)

| | SOURCE | MUG | INDOLE | GAS |
|---|---|---|---|---|
| 64 | Beach | − | + | − |
| 65 | Creek | +++ | + | + |
| 66 | Effluent | +++ | + | + |
| 67 | Effluent | − | + | + |
| 68 | Well*** | + | + | + |
| 69 | River | +++ | + | + |
| 70 | River | +++ | − | + |
| 71 | Well | ++ | + | + |
| 72 | Well | +++ | + | + |
| 73 | River | +++ | + | + |
| 74 | Lake | ++ | + | + |
| 75 | Dugout | +++ | + | + |
| 76 | Well | +++ | + | + |
| 77 | Well | +++ | + | + |
| 78 | Beach | − | + | + |
| 79 | Beach | +++ | + | + |
| 80 | Beach | +++ | + | + |
| 81 | Creek | +++ | + | + |
| 82 | Beach | + | + | + |
| 83 | Beach | +++ | + | + |
| 84 | Beach | − | + | + |
| 85 | Well*** | ± | + | + |
| 86 | Well*** | − | − | + |
| 87 | Well*** | +++ | − | + |
| 88 | Well*** | ++ | + | + |
| 89 | Pond | +++ | + | + |
| 90 | Effluent* | +++ | + | + |

*Chlorinated
**Untreated
***Pristine

Table 6 shows the results of E. coli detection with MMO-MUG and the current test performed on ninety water samples obtained from variety of environmental sources. Some samples were pristine (well), some samples were chlorinated, some samples were nontreated effluents. In majority of case, both MMO-MUG and the current indole test agreed. In samples obtaining MUG-negative E. coli, MUG was not able to detect the presence of E. coli.

Fifteen (17%) of the total 90 samples, namely samples 1, 10, 19, 34, 45, 48, 51, 52, 54, 60, 62, 64, 67, 78 and 84 were MUG-negative and indole-positive and contained E. coli. Insofar as the procedures used MUG and the current test respectively, MUG-negative E. coli were recognized by the current indole test, but not by the MMO-MUG test.

Three (3%) of the ninety E. coli isolates (Samples 47, 70, 87) were MUG-positive and indole-negative. These samples were recognized as E. coli by either MMO-MUG or by the medium I of the current invention which contains MUG. But they are not detectable by the medium I containing only ONPG, if the MUG was not added to that medium.

One (sample 86) of the 90 environmental E. coli isolates (1%) was both MUG-negative and indole-negative. This rare E. coli was not detected by either MMO-MUG or by current method.

From the above results, it is clear that for a routine water testing the current method is more valuable than MMO-MUG, as it is able to recognize both MUG-positive (60–70%) and MUG-negative, indole-positive E. coli (30–40%).

Testing of Medium III

Medium III composition which has the low pH and contains TMAO, is a nutritive medium compared to other media available in the prior art. It suitability was tested on E. coli laboratory isolates which were submitted to severe degree of chlorination of several (4–6) logs of bacteria killing so that all surviving E. coli were severely injured.

Then the samples of these chlorine injured isolates were submitted to comparative testing for the presence of E. coli. Standard lauryl tryptose test broth was used as a medium for total coliform standard methods LTB test.

Samples were run in series of five tubes per sample. Three independent experiments were performed. The incubation temperature for lauryl tryptose broth was 35° C. for 24 hours. Medium III of the current invention was used for two other testing groups having the same number of samples and experiments. One medium III group of samples was incubated at 35° C. for 24 hours. The second medium III group was incubated at 44.5° C. for 24 hours.

Group 2, medium III (35° C.) test for detection of severely chlorine injured E. coli was based on ONPG and MUG containing medium. No indole test was performed in this group. Incubation was at 35° C.

Group 3 utilizing medium III for specific detection of injured E. coli was performed at temperature of 44.5° C. and included ONPG, MUG, and indole test.

Figure 2:
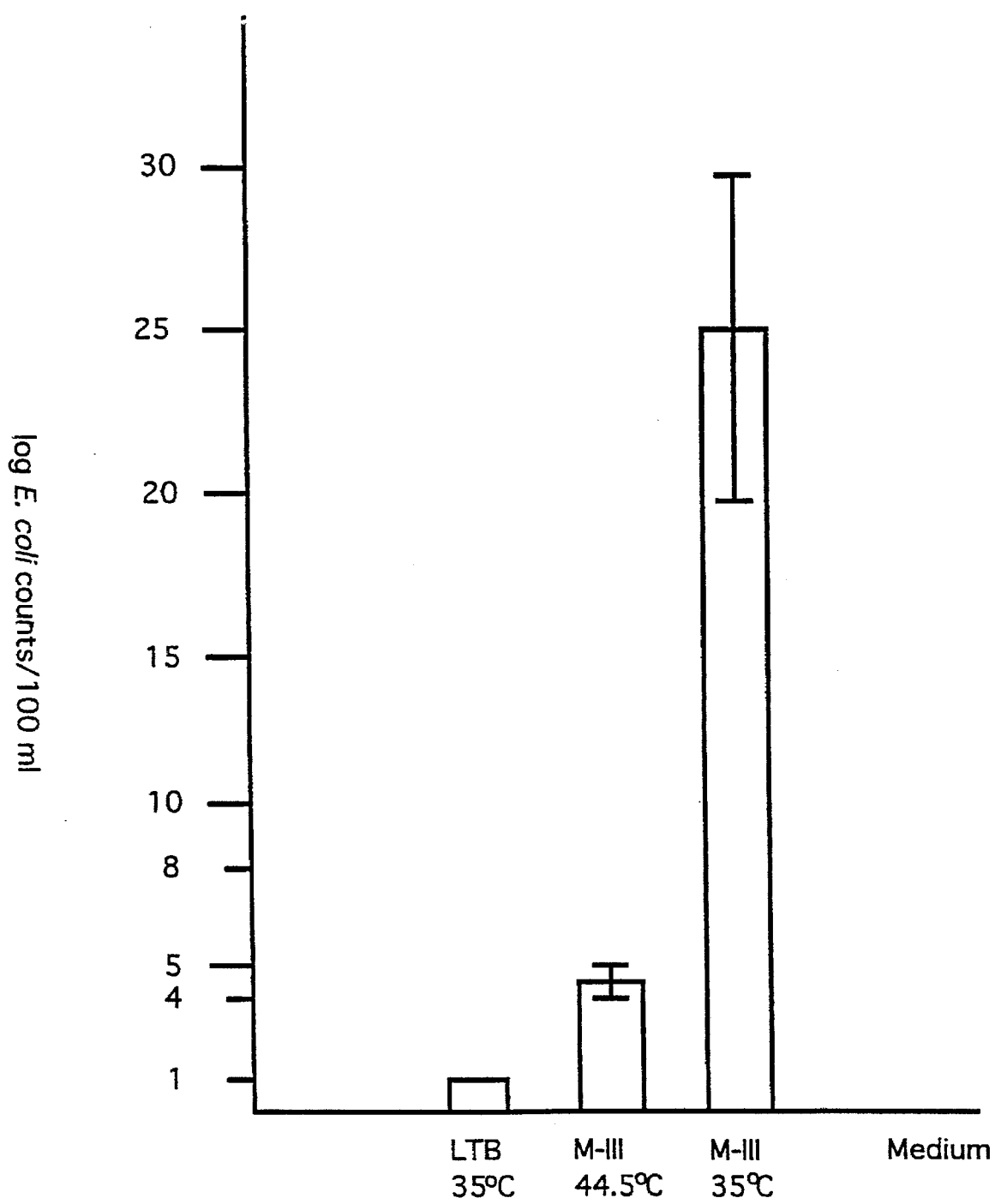
FIG. 2 is a graph showing a degree of injured E. coli detection by standard lauryl tryptose method and by the current method using medium III at 35° C. or 44.5° C.

Results are shown in FIGS. 1 and 2. FIG. 1 is the log graph expressing the counts of E. coli found in 100 ml of water containing chlorine injured E. coli. The lauryl tryptose test (LTB) results were normalized and expressed as log 100% E. coli counts per 100 ml. Medium III including indole test (Medium III 44.5° C.) was in an average 4.3× better than LTB at 35° C. and medium III at 35° C. had in an average 20–30 times better detection of chlorine injured E. coli than LTB at 35° C. These results show that the medium III of the current invention is an excellent medium for detection of injured E. coli. With increased temperature to 44.5° C. it loses some of its sensitivity, however, as the 44.5° C. temperature allows unequivocal detection of injured. E. coli by additional indole test, the certain degree of loss of sensitivity is overcome by increased specificity provided by indole test inclusion.

The reason for loss of sensitivity is quite obviously the higher temperature during the incubation which further kills the most injured E. coli. However, since the specificity of the method is increased substantially against the standard LTB test, by addition of indole test, such loss of sensitivity is not very important, particularly when the medium III at 44.5° C. is still able to detect about 4.3–4.5 times more E. coli than standard LTB test.

FIG. 2 illustrates the differences found in detection of injured E. coli by using various methods and mediums. The superior performance of medium III at 44.5° C. and particularly at 35° C. is clearly illustrated in FIG. 2.

Testing of Medium IV

Another method for detection of E. coli utilizes the fact that the coliform test is advantageous but not necessary for detection of E. coli when the medium IV, lacking both glucosides and glucuronides is used for detection of normal E. coli, chlorine or food processing injured E. coli in water, food or seafood samples. The indole test performed at 44.5° C. or, in alternative, at 35° C. for 4 hours at 44.5° C. for 20 hours, on samples containing laboratory isolates of E. coli turn purple upon addition of Kovacs reagent. Control samples which do not contain E. coli but contain coliform do not turn purple upon addition, of Kovacs reagent.

For injured E. coli bacteria whether by chlorination or by food processing, medium IV—variation (24) or other variations having an additional source of carbon and nitrogen are most suitable. Even slight *E. coli* contamination is detectable using these conditions.

The medium IV and method for *E. coli* detection is specifically designed to promote the growth of injured *E. coli* in this medium. This medium is particularly suitable to promote the growth of small number of coliform including injured *E. coli* cells present in highly diluted water samples and also for determination of the presence or absence of very small numbers and/or even one single coliform (including *E. coli*) cell.

UTILITY

The media and methods of the current invention represent a completely new approach to the detection of *E. coli* in water, food or seafood samples. Medium constituents which are specifically designed to promote the growth of coliforms including *E. coli*, and particularly these bacteria which are present in small numbers or are weakened or injured. For the first time, the composition of the *E. coli* detection medium recognizes and overcomes a substrate suppression of indole production in growing cells which is caused by lactose or lactose substitutes and provides optimal nutrient medium promoting *E. coli* growth and recovery from injury.

The current invention is suitable for detection of *E. coli* in water, food or seafood. Because of its high sensitivity and specificity, the method is particularly suitable for detection of *E. coli* in diluted water samples where the *E. coli* contamination is minute and would not be detectable by methods currently available. The method and the used media are designed to address problems currently observed with other detection methods. The medium provides the substrate for detection of both MUG-positive and MUG-negative *E. coli*. The media, in any of the variations but particularly when medium II, III, and IV are used are *E. coli* recovery and growth promoting. The current media are not minimum nutrients media but are design to be nutritive or highly nutritive. Nutrients supplied by the media are specifically chosen to promote *E. coli* and no other bacteria growth and recovery.

The media are easily prepared and can be stored for almost unlimited time in liquid, dry, frozen or freeze dried form. Quantitation and kits for detection of *E. coli* and for *E. coli* enumeration are described in Examples.

The above described and other embodiments falling within the scope of this invention are contemplated to be claimed.

MATERIALS

Ehrlich's Reagent, p-dimethylaminobenzaldehyde in acidified n-butyl alcohol (Sigma); Kovacs Reagent, p-dimethylaminobenzaldehyde in acidified isoamylalcohol (Sigma); tryptophan (Sigma); tryptose (Difco), o-nitrophenyl-β-D-galactopyranoside (Sigma) sodium lauryl sulfate (Sigma); isopropyl β-D-thiogalactopyranoside (Sigma); yeast extract (Difco), L-glutamate (or Sigma Cal Biochem).

EXAMPLE 1

A Method for Determination of Presence or Absence of Total Coliform and *E. coli* in Water Samples This example illustrates the method for quick visual coliform *E. coli* test determination of presence or absence of *E. coli* and/or coliform in water samples. The method utilizes distinct characteristics specific to coliform and *E. coli*, namely ability to utilize lactose (coliform) and lactose utilization and formation of indole (*E. coli*). Bacteria used in this example were from grown colonies supplied but not those actually appearing in water samples.

The principle of this method is that the lactose which normally inhibits formation of indole, is substituted with another substrate which is metabolized or utilized in the same manner as lactose, by the enzyme β-galactosidase. The substitute for lactose does not inhibit formation of indole from tryptophan, consequently, when the yellow color develops, the sample contains coliforms and may or may not contain *E. coli*. When there is no yellow color present, there is no coliform and no *E. coli* present.

For this method, a specific tryptophan-galactosidase medium I variation 3 containing minimal amounts of tryptophan and lactose-substitute ONPG was prepared and used. Medium optionally has isopropyl-β-D-thiogalactopyranoside (IPTG), lactose production inducer, and was prepared in distilled water.

Pre-sterilized 20 ml bottles containing 3 ml of concentrated medium were inoculated with 1000 bacterial cells in 0.010 ml 0.85%. Samples were divided as follows.

Samples 1–8 were pure *E. coli:*
1 and 2 were ATCC 25922
3 and 4 were ECOR 4
5 and 6 were ECOR 5
7 and 8 were ECOR 6
  Expected results: ONPG-positive; indole positive.
  Samples 9–14 were Non-*E. coli* coliform:
9 and 10 were *Enterobacter cloacae*
11 and 12 were *Citrobacter freundii*
13 and 14 were *Klebsiella pneumoniae*
  Expected results: ONPG-positive; indole-negative.
  Samples 15 and 16 were other non-coliform bacteria:
15 and 16 were *Salmonella*
  Expected results: ONPG-negative; indole negative.

The bottles were closed and gently shaken so that the samples with the medium were properly mixed. The bottles were put in an incubator at 35° C. for 18 hours incubation. Following the incubation, samples were visually examined.

Results corresponded to expected results.

Before addition of Kovacs reagents, control Samples 15 and 10 remained colorless, indicating that there were no coliform and *E. coli* present. *E. coli* samples 1–14 were bright yellow, coliforms were present and had grown to large numbers indicating the presence and subsequent growth of coliform bacteria.

Addition of few drops of Kovacs reagent to tubes 2, 4, 6, 8–16 resulted in development of a purple color in samples 2, 4, 6, and 8, which were *E. coli* but not in samples 9–14 which were non-*E. coli* coliform or in samples 15–16 which were non-*E. coli* non-coliform bacteria. The development of purple color coliforms that samples 2, 4, 6, and 8 were *E. coli*. In this experiment, samples 1, 3, 5, and 7 which were also *E. coli* were not submitted to Kovacs reagent in order to illustrate the difference between sole ONPG substrate test, such as used currently and known as Colilert Test and between the current test proving the presence of indole.

This is a coliform and *E. coli* presence/absence method. The yellow color and indole test indicates that both lactose utilization and indole production characteristic for *E. coli* were present in samples 1–8. The yellow color and negative indole tests of samples 9–14 evidenced the presence of coliforms other than *E. coli*. Absence of any color indicated the absence of both *E. coli* and coliform.

EXAMPLE 2

Quick Test—A Kit for Determination of Coliform and *E. Coli* in Water Samples

Summary

*E. coli* presence in the water is generally recognized as evidence of sewage contamination.

E. coli is a species of family *Enterobacteriaceae*. *E. coli* possess two characteristics: lactose utilization, and indole production distinguishing it from other *Enterobacteriaceae* and other coliforms.

In detection of *E. coli*, current QUICK TEST utilizes these two characteristics and determines the presence of β-galactoside, an enzyme involved in lactose utilization and the presence of tryptophanase, an enzyme involved in indole production. In detection of *E. coli* presence, water samples are reacted with current QUICK TEST medium containing tryptophan and o-nitrophenyl-β-galactopyranoside (ONPG) at 35° C. until a yellow color develops at 18 hours. The presence of the yellow color indicates both a lactose utilization. Indole formation is determined with Kovacs reagent as a red-purple color. The presence of the yellow color in water phase indicates lactose utilization and the presence of red-purple color indicates the indole formation and both indicates the presence of *E. coli* in tested water samples.

PRODUCT DESCRIPTION, STORAGE

QUICK TEST consisting of:

3 sterile glass vials having a line at 100 ml level with stoppers of 200 ml volume containing 50 ml of concentrated freeze-dried Medium each.

Concentrated Base Medium I contains 3 g of tryptophan, 1.5 g of ONPG, 0.3 g of isopropyl-β-D-thiogalactopyranoside (ITPG) 9 g sodium chloride, 0.3 g magnesium sulfate, 1.5 g potassium diphosphate, 9 g disodium phosphate, and 0.9 g sodium lauryl sulfate dissolved in distilled water. Sterilized.

Vial with Kovacs reagent with droppers.

Store the QUICK TEST in the refrigerator at 2°–8° C. until used. Do not open glass vials until ready to use.

SPECIMEN

Water sample to be tested-undiluted.

TEST PROCEDURE

Principle: Tryptophan in the medium provides a nitrogen source for *E. Coli* and is metabolized by *E. coli* tryptophanase to form free indole, pyruvate and ammonia in equimolar amounts. ONPG substituting for lactose is metabolized with β-galactosidase. At 35° C. *E. coli* grow and utilize ONPG and produce indole. β-galactoside turns the medium yellow. Since the tryptophan is used as the sole nitrogen source, no other bacteria than coliform and *E. coli* will produce the yellow color under these conditions. Upon addition of Kovacs reagent, the solution turns purple-red when *E. coli* is present.

SET-UP

Remove the vials with medium from the refrigerator, open the vial and add the water sample up to 100 ml mark on each vial. Close vials with the stoppers, swirl the vials gently so that the medium and water mix. Incubate at 35° C. until a bright yellow color develops or 24 hours whatever is shorter. Record. Incubate the second vial for 4 hours at 35° C. followed by 20 hours at 44.5° C. Add 2–3 drops of Kovacs reagent, mix, let stand for 10 seconds. Observe. Record purple-red color which may develop immediately.

EVALUATION OF RESULTS

Bright yellow color of the solution incubated at 35° C. signifies the presence of coliform. The red-purple color signifies the presence of *E. coli*. Yellow in the 44.5° C. tube indicates fecal coliform. No change in color signifies the absence of *E. coli*, fecal coliforms, or coliforms.

EXAMPLE 3

Method for Determination of Total Coliform and *E. Coli*

This example illustrates the determination of total coliform and *E. coli* present in diluted water samples by utilizing tryptophan as one nitrogen source, another nitrogen containing compound as the second nitrogen source and lactose substitute for determination of β-galactosidase. Under these conditions, most *Enterobacteriaceae* grow, all coliforms give yellow color and *E. coli*, distinguished by indole production, give red-purple color with either Kovacs's or Ehrlich reagent.

Preparation for Normal Medium Base (4)

1 g of tryptophan, 0.5 g of ONPG, 1 g of tryptose, 0.1 g of sodium lauryl sulfate, 0.1 g of isopropyl-β-D-thiogalactopyranoside and sodium chloride up to 50mmol, 0.1 g $MgSO_4$, 0.5 g $KH_2PO_4$, 3 g $Na_2HPO_4$ are dissolved in 1000 ml of distilled water and sterilized at 121° C. for 15 minutes. The ONPG and IPTG are added as a filter sterilized solution.

Preparation of Concentrated Medium Base (5)

This medium is like the Normal Medium except that all ingredients are 3 times as concentrated. For use in Presence-absence tests, this medium is prepared in 50 ml portions in sterile bottles. Then 100 ml of water sample are added, the sterile caps reapplied, and the bottles incubated at 35° C. for 24 hours.

Incubate a similar bottle at 35° C. for 4 hours and transfer it to a 44.5° C. water bath for 20 hours.

After the incubations are completed, interpret the results as in the previous example:

35° C. incubation: yellow color: total coliform present;

no yellow color: absence of total coliforms.

44.5° C. incubation: yellow color: presence of fecal coliform(s);

no yellow color: absence of fecal coliforms;

red color upon addition of Kovacs' reagent: presence of *E. coli*.

Experimental Samples

Sixteen sterile glass 30 ml vials were prepared and marked 1–16. Into these pre-sterilized vials containing 30 ml of freeze-dried concentrated medium base (5) was noculated with 1000 bacterial cells in 0.010 ml 0.85% saline 20 sample to be tested.

Samples 1–8 were *E. coli:*
1 and 2 were ATCC 25922
3 and 4 were ECOR 4
5 and 6 were ECOR 5
7 and 8 were ECOR 6

Samples 9–14 were Non-*E. coli* coliform:
9 and 10 were *Enterobacter cloacae*
11 and 12 were *Citrobacter freundii*
13 and 14 were *Klebsiella pneumoniae*

Samples 15 and 16 were non-coliform bacteria:
15 and 16 were *Salmonella*

The bottles were closed and gently shaken so that the samples with the medium were properly mixed. The bottles were put in the water bath at 35° C. for 18 hours incubation. Following the incubation, next morning the samples were visually examined.

Results

Control samples 15–16 remained colorless showing that neither coliform nor *E. coli* were present. Coliform only samples 9–14 were bright yellow showing that various coliform were present, however, at this point it was not clear whether any *E. coli* were present in samples 9–14. Samples 1–8 containing *E. coli* only were also bright yellow suggesting that there were either coliform and/or *E. coli*. Again, at this point it was unclear whether only coliform, only *E. coli*, or both were present in samples 1–8.

Samples 1–14 were then investigated for the presence of free indole.

A set of 14 small sterile petri dishes were prepared and 1 ml of solution from vials 1–14 was transferred to these dishes. Filter paper saturated with Kovacs reagent was placed over the petri dish. After 4 hours, the filter was examined for purple red color or spots.

Results

The filters placed over petri dishes 9–14 were not stained and remained white, indicating the absence of *E. coli*. Filters 1–8 had a purple red color spots evidencing the presence of *E. coli* colonies.

EXAMPLE 4

Rapid E.C. Test—A Kit for Determination of Total Coliform and *E. Coli* in Water Samples Summary Coliform bacteria are those *Enterobacteriaceae* that can produce gas or acid from lactose in certain media. *E. coli* as well as other environmental bacteria. Only *E. coli* presence in the water is generally recognized as evidence of sewage contamination.

*E. coli* is a species of family *Enterobacteriaceae*. *E. coli* possess two characteristics: lactose utilization, and indole production distinguishing it from other *Enterobacteriaceae* and other coliforms.

In detection of total coliform and *E. coli*, RAPID TEST utilizes these two characteristics and determines the presence of β-galactosidase, an enzyme involved in lactose utilization which appear in coliforms including *E. coli* and tryptophanase, an enzyme involved in indole production, which appear only in fecal *E. coli*. In detection of total coliform, the yellow color derived from β-galactosidase metabolizing ONPG-lactose substitute is observed. In this test, water samples are reacted with RAPID TEST medium containing tryptophan and o-nitrophenyl-β-galactopyranoside (ONPG), tryptose, sodium lauryl sulfate, isopropyl-β-D-thiogalactopyranoside and sodium chloride at 35° C. for 4 hours and 44.5° C. for 20 hours. The presence of a yellow color indicates a lactose utilization of lactose surrogate ONPG with β-galactosidase. The presence of yellow color indicates the presence of fecal coliforms including *E. coli*. Samples containing yellow color are subsequently submitted to indole test, wherein small portion of a yellow colored sampled from step 1 is reacted with Kovacs reagent. Only those samples which give purple-red color contain *E. coli*. Indole formation evidenced by purple red color thus indicates the presence of *E. coli* in tested water sample.

PRODUCT DESCRIPTION, STORAGE

RAPID TEST consisting of:

Step 1: 2 sterile glass vials of 20 ml volume with stoppers containing 3 ml of concentrated freeze-dried Medium each.

Concentrated Base Medium I contains 3 g of tryptophan, 1.5 g of ONPG, 3 g of isopropyl-β-D-thiogalactopyranoside (ITPG), 9 g of tryptose, and 0.3 g of sodium lauryl sulfate 0.3 g magnesium sulfate, 1.5 g potassium diphosphate, 9 g disodium phosphate, 9 g sodium chloride dissolved in 1000 ml distilled water. Sterilized.

Store the RAPID TEST in the refrigerator at 2°–8° C. until used. Do not open glass vials until ready to use.

Step 2: Dropping bottle containing Kovacs reagent.

SPECIMEN

Water sample to be tested-undiluted.

TEST PROCEDURE

Principle of Step 1: ONPG substituting for lactose is metabolized with β-galactosidase. At 44.5° C. *E. coli* grow and utilize ONPG and produce indole. β-galactoside turns the medium yellow. In the yellow colored medium, both fecal coliforms and *E. coli* are present. In samples which do not have a yellow color, there are no fecal coliforms and *E. coli*.

Principle of Step 2: Tryptophan in the medium is metabolized by *E. coli* tryptophanase to form free indole, pyruvate and ammonia in equimolar amounts. At 44.5° C. in the presence of lauryl sulfate, nitrogen source, no other bacteria than *E. coli* will produce the purple-red color when the Kovacs reagent is added.

SET-UP

Remove the vials with freeze-dried medium from the refrigerator, open the vial and add the water sample up to 100 ml mark on the vial. Close the vial with the stopper, swirl the vial gently so that the medium and water mix. Incubate at 35° C. for 4 hours and 44.5° C. for 20 hours.

Separate vials having no color from those having a yellow color.

Add a drop of Kovacs' reagent to each yellow colored vial and look for the formation of purple-red color within 10 seconds. Record.

EVALUATION OF RESULTS

Step 1

Bright yellow color of the samples signify presence of a fecal coliform and may or may not include *E. coli*. No change in color signifies absence of fecal coliforms and *E. coli*.

Step 2

Red-purple color of the sample after addition of Kovacs reagent signifies the presence of free indole and thus the presence of *E. coli*. Absence of red-purple color signifies the absence of *E. coli* but presence of coliform.

EXAMPLE 5

Multiple Tube Dilution Assay

This example illustrates enumeration method for determination of the most probable number of *E. coli* present in the water sample.

The method is based on the sequential dilution method generally used in the microbiological testing. Water samples are diluted by several orders to determine the most probable number of E. coli.

This example illustrates the method for quick visual determination of presence or absence and enumeration of E. coli in water samples. The method utilizes two distinct characteristics specific to E. coli., namely utilization of lactose and formation of indole.

The principle of this method is that the lactose which normally inhibits formation of indole, is substituted with substrate which is metabolized or utilized by the same enzyme as lactose, by namely β-galactosidase. In this manner, the substitute for lactose does not inhibit formation of indole from tryptophan.

For this method, a specific tryptophan-galactosidase medium III containing tryptophan, and a lactose substitute ONPG was prepared and used. The medium optionally has isopropyl-β-D-thiogalactopyranoside (IPTG), a β-galactosidase inducer, and tryptose as a secondary nitrogen source and is preferably prepared in a suitable mineral salts solution. The medium is reacted with normal and diluted samples. From the degree of dilution, the most probable number of E. coli present can be determined.

Procedure for determination of E. coli and fecal coliforms by multiple fermentation tube, "most probable number" (MPN) method.

Use medium I or preferably medium III in the standard methods protocol (Standard Methods of Analysis of Water and Waste Water, 17th edition, American Water Works Association, American Public Control Foundation). In brief summary, add five 10 ml portions of water sample to tubes containing 10 ml of double-strength medium. Add five 1.0 ml portions of sample to five tubes containing 9 ml of single strength medium. Add view 0.1 ml portions of sample to additional tubes containing 9 ml medium. Then dilute the original sample and make additional inoculations as necessary to give a series of 5-tube sets, each containing a different portion of sample.

Incubate the tubes for 4 hours at 35° C. and then 20 hours at 44.5° C. Inspect for yellow color (ONPG test for fecal coliforms), fluorescence (MUG test for MUG-positive E. coli), and red color upon addition of Kovacs' reagent (indole test for E. coli). Record results and use a most probable number table to estimate the fecal coliforms, MUG-positive E. coli, and E. coli count in the original sample.

Procedure for Determination of E. Coli

For each sample, the set of five sterile tubes in triplicate was prepared and marked 1A, 1B, 1C, 2A, 2B, 2C, 3A, 3B, 3C, 4A, 4B, 4C and 5A, 5B, 5C; and other description of the sample such as I, II, etc. Each tube has a saline at 10 ml volume.

There were 3 samples for each group
I Controls—containing Salmonella
II E. coli ATCC 25922, ECOR 4, ECOR 5 and ECOR 6
III Coliforms without E. coli, Klebsiella pneumoniae, Citrobacter freundii, Enterobacter cloacae.

Into each of the tubes I 1A–I 5A, II 1A–II 5A, III 1A–III 5A, etc., 10 ml of the media (6) was added up to the line on the tube. Then, 1 ml of sample to be tested was added to tubes 1A, and 1B, 1C to achieve 1/10 dilution. Mixed. 1 ml of solution from tube 1A was removed and transferred to the tube 2A to achieve 1/100 dilution. Mixed. 1 ml of solution from tube 2A was removed and transferred to the tube 3A to achieve 1/1,000 dilution. Mixed. 1 ml of solution 3A was removed and transferred to the tube 4A to achieve dilution 1/10,000. Mixed. 1 ml of solution from the tube 4A was transferred to the 5A to achieve dilution 1/100,000 tubes 1B–5B and 1C–5C were prepared in similar way.

Coliform samples III and E. coli samples II were similarly diluted.

Alternatively, one will make serial dilutions in saline or 0.1% peptone and then put 0.1 or 1.0 ml of each dilution into each of three culture tubes.

Tubes were closed or covered and gently shaken so that water with the medium were properly mixed. The tubes were put in a 35° C. incubation for 24 hours incubation. Following the incubation, samples were visually examined.

Results

Control samples of Group I remained colorless, there were no coliforms or E. coli present. E. coli samples of group II were bright yellow, and after adding Kovacs reagent were red-purple. E. coli were present in large number in tubes II 1A, B, C–3A, B, C. Coliform samples of group III were pale yellow suggesting the presence of coliform. There: was slightly visible purple color in samples II 4, A, B, C–5, A, B, C.

This is a E. coli multiple dilution method. The red-purple color indicates that both lactose utilization and indole production characteristic for E. coli are present anal thus the presence of E. coli is determined. The number of positive tubes at each dilution, when interpreted with a most-probable number (MPN) table, gives an estimate of the concentrations of coliforms and E. coli in the original samples.

EXAMPLE 6

Test—A Kit for Quantitation of E. Coli in Water Samples

E. coli presence in the water is generally recognized as evidence of sewage contamination. Under the present regulations issued by EPA, the current permissible level of contamination of drinking water is zero E. coli/100 ml of water. If the fecal E. coli is present, it shows up within the coliform group. However, not all coliforms are of fecal origin and thus it is necessary to determine the approximate most probable number of E. coli present within the coliforms.

E. coli is a species of family Enterobacteriaceae and is one of the coliforms. E. coli possess two characteristics: lactose utilization, and indole production distinguishing it from other Enterobacteriaceae and other coliforms.

In detection of most probable number of E. coli, the test utilizes these two characteristics and determines the presence the yellow or red-purple color in 10 fold diluted sequence of samples. In detection of E. coli presence, water samples are sequentially diluted and reacted with medium III containing essentially tryptophan and o-nitrophenyl-β-galactopyranoside (ONPG) and reaction enhancers at 35° C. for 4 hours and 44.5° C. for 20 hours. The presence of a yellow color indicates the presence of fecal coliforms and/or E. coli in tested water sample. After reaction with Kovacs reagents, the red-purple color develops in samples containing E. coli. The number of E. coli depends on the dilution.

PRODUCT DESCRIPTION, STORAGE

Quantitative Test consisting of:

For one sample:

15 sterile tubes with stoppers having a line at 10 ml level containing originally 10 ml of concentrated freeze-dried Medium Base each. Marked x for sample identification and subdivided, into 1A–5A, 1B–5B, 1C–5C.

Concentrated Base Medium III contains 3 g of tryptophane, 1.5 g of ONPG, 3 g of isopropyl-β-D-thiogalactopyranoside, 0.3 g of sodium lauryl sulfate dissolved in mineral salts at 3 times the usual concentration. Sterilized.

Dropping vial with Kovacs reagent.

Store the quantitative test in the refrigerator at 2°–8° C. until used. Do not open glass tubes until ready to use.

SPECIMEN

Water sample to be tested-undiluted.

TEST PROCEDURE

Principle: Tryptophan in the medium is metabolized by $E.$ $coli$ tryptophanase to form free indole, pyruvate and ammonia in equimolar amounts. ONPG substituting for lactose is metabolized with β-galactosidase. At 44.5° C. $E. coli$ grow and utilize ONPG and produce indole. The action of β-galactosidase on ONPG turns the medium yellow. Under these conditions, only $E. coli$ will produce the yellow color and will turn red-purple with Kovacs reagent.

SET-UP

Remove the tubes with freeze-dried medium from the refrigerator, open the tube and add the water sample up to 10 ml mark on the vial.

Incubate 4 hours at 35° C. followed by 20 hours at 44.5° C. Record the presence or absence of yellow color, fluorescence, and red color after addition of 2–3 drops of Kovacs reagent.

EVALUATION OF RESULTS

Bright yellow color of the solution signifies presence of fecal coliform and/or $E. coli$. Fluorescence or red-purple color signifies presence of $E. coli$. No change in color signify absence of $E. coli$.

Dilution:

For evaluation, use a standard 10-tube MPN table to estimate the fecal coliform and $E. coli$ count.

EXAMPLE 7

Membrane Filter Techniques

This example illustrates another methodological variation for the current tests.

Materials:

Sterile membrane filters. Examples, recommended in various Standard Methods publications, include 47 mm, 0.45 m plain or gridded membranes such as Gelman GN6. Hydrophobic grid membrane filters (HMGF) can also be used.

Filter Apparatus:

A suitable sterilizable or pre-sterilized disposable filter funnel and flask. Also a manual or electrical device for drawing a water sample through the membrane filter.

Medium:

Liquid medium III is kept from flowing by incorporation into a gel (typically a 1.5% agar gel) or by saturation of a sterile filter paper pad (typically 2 ml of medium on a 55 mm diameter pad). The medium III is pre-sterilized and held in a suitable sterile container such as a petri dish.

Typical Use:

A 100 ml water sample is filtered through the membrane filter, using the filter apparatus. The filter is removed with sterile forceps and placed carefully onto a pad saturated with 2 ml of medium III. The medium III containing 0.1 g X-GAL is used in place of 0.5 g ONPG per 1000 ml of medium.

The filter pad, and medium are incubated inside the protecting petri dish at 35° C. for 4 hours and at 44.5° C. for 20 hours. The colonies are inspected and the blue ones or fluorescent are noted. These are coliforms.

To determine which coliform colonies are $E. coli$, the membrane filter to a filter are transferred paper pad saturated with Kovacs' reagent.

If after two minutes, a reddish tint appears, indicates a colony of indole-positive bacteria. Indole-positive coliforms are $E. coli$. For easier view of the reddish color the filter is gently lifted and inspecting on the bottom side.

Data Collection:

The number of blue colonies is the coliform count in colony-forming units (cfu) per 100 ml. The number of blue colonies which turn reddish upon contact with Kovacs' (or Ehrlich's) reagent is the $E. coli$ count in cfu per 100 ml.

We claim:

1. A method for detecting coliform and $E. coli$ bacteria in a water or food sample comprising a plurality of different bacteria, which method comprises steps:

(a) contacting said bacteria of said sample with a medium comprising:
      (i) a β-D-galactosidase substrate;
      (ii) a tryptophanase substrate;
      (iii) a protein or peptide hydrolysate in an amount sufficient to promote the growth of $E. coli;$
   (b) incubating said bacteria at a temperature of 44.5° C. for 2 to 48 hours; then
   (c) determining a presence or absence of a β-D-galactosidase reaction detectable product of said β-D-galactosidase substrate;
   (d) determining the presence or absence of a tryptophanase reaction detectable product of said tryptophanase substrate;

wherein the presence of said β-D-galactosidase reaction product indicates the presence of a coliform bacterium in said sample and the presence of said tryptophanase reaction product indicates the presence of an $E. coli$ in said sample.

2. A method according to claim 1, wherein the presence or absence of at least one of said β-D-galactosidase reaction product and said tryptophanase reaction product is determined by color change.

3. A method according to claim 1, wherein at least one of said β-D-galactosidase substrate and said tryptophanase substrate is chromogenic or fluorogenic.

4. A method according to claim 1, wherein at least one of said β-D-galactosidase reaction product and said tryptophanase reaction product is detected by chemical analysis.

5. A method according to claim 4, wherein said chemical analysis comprises chemically reacting said tryptophanase reaction product with a tryptophanase reaction product detection reagent comprising p-dimethylaminobenzaldehyde, to produce a spectrophotometric signal.

6. A method according to claim 1, further comprising filtering said sample through a microporous filter prior to said contacting step.

7. A method according to claim 6, wherein said bacteria are contacted with said medium by contacting said filter comprising said bacteria with said medium, whereby said medium is absorbed into said filter.

8. A method according to claim 6, wherein said medium is incorporated into a gel.

9. A method according to claim 6, wherein at least one of said β-D-galactosidase reaction product and said tryptophanase reaction product is insoluble in said medium.

10. A method according to claim 6, wherein said β-D-galactosidase substrate is X-Gal.

11. A method according to claim 1, wherein said hydrolysate is a peptone.

12. A method according to claim 1, wherein said hydrolysate is tryptose.

13. A method according to claim 1, wherein said hydrolysate is a yeast extract.

14. A method according to claim 1, wherein said medium further comprises an inhibitor of bacterial growth selected from the group consisting of a detergent, an antibiotic, and a bile salt.

15. A method according to claim 1, wherein said medium further comprises an inducer of β-D-galactosidase.

16. A medium for detecting coliform and E. coli bacteria in a water or food sample comprising a plurality of different bacteria, which medium comprises:

(i) a β-D-galactosidase substrate;

(ii) a tryptophanase substrate;

(iii) a protein or peptide hydrolysate in an amount sufficient to promote the growth of E. coli;

(iv) an inhibitor of bacterial growth selected from the group consisting of a detergent, an antibiotic, a toxic dye, bile salts;

wherein at least one of said β-D-galactosidase substrate and said tryptophanase substrate is chromogenic or fluorogenic.

17. A medium according to claim 16 further comprising:

(v) a trimethylamine oxide reductase substrate.

18. A kit for detecting coliform and E. coli bacteria in a water or food sample comprising a plurality of different bacteria, which kit comprises a premeasured amount of a medium comprising:

(i) a β-D-galactosidase substrate;

(ii) a tryptophanase substrate;

(iii) a protein or peptide hydrolysate in an amount sufficient to promote the growth of E. coli;

(iv) an inhibitor of bacterial growth selected from the group consisting of a detergent, an antibiotic, a toxic dye, bile salts;

wherein at least one of said β-D-galactosidase substrate and said tryptophanase substrate is chromogenic or fluorogenic.

19. A kit according to claim 18 wherein said medium further comprises:

(v) a trimethylamine oxide reductase substrate.

* * * * *